United States Patent [19]

Rubin et al.

[11] Patent Number: 5,260,210
[45] Date of Patent: Nov. 9, 1993

[54] BLOOD-BRAIN BARRIER MODEL

[76] Inventors: Lee L. Rubin; Seth Porter; Heidi C. Horner; Theodore A. Yednick, all of Athena Neurosciences, Inc., 800F Gateway Blvd., So. San Francisco, Calif. 94080

[21] Appl. No.: 577,650

[22] Filed: Sep. 4, 1990

Related U.S. Application Data

[63] Continuation-in-part of Ser. No. 413,274, Sep. 27, 1989.
[51] Int. Cl.$^5$ .............................................. C12N 5/06
[52] U.S. Cl. ......................... 435/240.23; 435/240.24; 435/240.241; 435/240.242; 435/240.243
[58] Field of Search ........... 435/240.2, 240.21, 240.23, 435/240.24, 240.241, 240.242, 240.243

[56] References Cited

U.S. PATENT DOCUMENTS 4,208,406  6/1980  Lapinet .
4,764,504  8/1988  Johnson .

OTHER PUBLICATIONS

Audus, et al., Pharmaceutical Research, vol. 3, No. 2, pp. 81–87, 1986.
Van Bree, et al., Pharmaceutical Research, vol. 5, No. 6, pp. 369–371, 1988.
Arthur, et al., Developmental Brain Research, vol. 36, pp. 155–159, 1987.
Janzer, et al., Nature, vol. 325, pp. 253–257, 1987.
Kruse, Jr., et al. (Editors) Tissue Culture, Methods and Applications, Academic Press, New York, 1973, pp. 372–377.
Freshney, Culture of Animal Cells, Annual of Basic Technique, Alan R. Liss, Inc., New York, 1983, pp. 55–59.
Kumagai, K. K., et al., J. Biol. Chem., 262:15214 (1987).
Audus, K. L., et al., Ann. N.Y. Acad. Sci., 507:509 (1987).
Van Bree, J.B.M.M., J. Pharm. Exp. Therap., 247:1233 (1988).
Hart, M. N., J. Neuropath. Exp. Neurol., 46:141 (1987).
Rutten, M. J., Brain Res., 425:301 (1987).
Tao-Cheng, J. -H., et al., J. Neurochem., 7:3293 (1987).
Arthur, F. E. Dev. Brain Res., 36:155 (1987).
Dehouck, M. -P., et al., J. Neurochem., 54:1798 (1990).
Springer, T. A., Nature, 346:425 (1990).
Tuomanen, et al., J. Exp. Med., 170:959 (1989).
Elices, et al., Cell, 60:577 (1990).
Pierschbacher and Ruoslahti, PNAS-USA 81:5985-5988 (Oct. 1984).
van Wezel, Microcarrier Cultures of Animal Cells, in Tissue Culture, Methods and Applications (Kruse and Patterson, eds.,), Academic Press, New York, 1973, pp. 372–366.
Grumbiner, et al., J. Cell Biol. 107:1575–1587 (Oct. 1988).
Duffey, et al., Nature 294:451–453 (Dec. 1981).
Chemical Abstracts, 105:350–47j, Audus, et al., Characterization of an In Vivo Blood-Brain Barrier Model System for Studying Drug Transport and Metabolism. (Abstract of Pharm. Res. 3:81-87 (1986).
Chemical Abstracts 113:57012m, Schwartz et al. (full paper J. Clin, Invest. 85:2019-2022 (1990).
Chemical Abstract 109:66314f (Van Bree, et al., Pharm. Res. 5:369-371 (1988).

Primary Examiner—Y. Christina Chan
Assistant Examiner—George C. Elliott

[57] ABSTRACT

An in vitro model of a blood-brain barrier comprising a porous solid support upon which is disposed an essentially confluent monolayer of brain microvascular endothelial cells in contact with agents that elevate effective cyclic AMP concentrations in endothelial cells, with or without astrocyte-derived or endothelial cell-derived conditioned medium or the equivalent so that high electrical resistance tight junctions are formed between endothelial cells, and endothelial cells exhibit peripheral phalloidin staining and E-cadherin. Also disclosed is the use of agents that reduce effective cyclic AMP concentrations or interfere with the functioning of cyclic AMP or increase effective cyclic GMP concentrations to open up blood-brain barriers in vitro and in vivo, so that drugs normally excluded by such barriers may substantially penetrate such barriers. Also disclosed are uses of the model to screen for reagents with clinical utility in disorders involving brain endothelial cells.

81 Claims, 11 Drawing Sheets

BLOOD-BRAIN BARRIER MODEL

This is a continuation-in-part of U.S. Ser. No. 097/413,274, filed Sep. 27, 1989.

BACKGROUND OF THE INVENTION

1. Field of the Invention

The present invention relates generally to in vitro models of endothelial cells. More particularly, the invention relates to an in vitro model that simulates the characteristics of microvascular endothelial cells of the brain that constitute the blood-brain barrier.

2. Description of Related Art

The vertebrate brain has a unique capillary system unlike that of any other organ of the body. This unique capillary system has morphological and biochemical characteristics that make up the "blood-brain barrier" (BBB). The BBB acts to separate the brain interstitial space from the blood. This barrier prevents molecules in the blood that are neither lipophilic or transported by specific carrier proteins from entering the brain (Betz, A. L. et al., *Ann. Rev. Physiol.*, 48:241 (1986); Pardridge, W. M., *Ann. Rev. Pharmacol. Toxicol.*, 28:25 (1988)).

The characteristics of the brain capillaries that make up the BBB include: (a) high-resistance tight junctions between endothelial cells of the brain that block transport of molecules between cells; and (b) limited amount of transport across cells, as compared to that occurring in peripheral capillaries.

The tight junctions of the BBB prevent passive diffusion of molecules and ions around the endothelial cells. Thus, most hydrophilic drugs and peptides that gain ready access to other tissues of the body are barred from entry into the brain, or their rates of entry are low. Thus, at the BBB, the only substances that can readily pass from the luminal core of the capillary to the abluminal tissue that surround the capillary are those molecules for which selective transport systems exist in the endothelial cells, as well as compounds that are lipid soluble. Such compounds, because of their inherent lipophilicity, are able to intercalate into the plasma membrane of endothelial cells and move to the abluminal side. These unique properties of the BBB have provided a major hindrance to the development of therapeutic agents directed toward diseases of the central nervous system (CNS), e.g., Alzheimer's disease and Parkinson's disease.

There are two general situations in which the ability to test for CNS entry of therapeutic agents is important. First, the increasing prevalence of CNS disorders and the introduction of new molecular biological and biochemical techniques to treat such disorders will lead to the development of new drugs that will be centrally active. These drugs must be tested for their ability to reach the brain, i.e., penetrate the BBB. Second, many drugs used to treat peripheral disorders have undesirable CNS side effects. As replacements for these drugs are developed, they will have to be screened for CNS penetration as well. Of course, the objective in that case is to develop peripherally-acting drugs that do not enter the brain.

Screening batteries of compounds for passage into the brain by conventional techniques is impractical. Generally, compounds are introduced into the carotid artery, and their concentration in the brain is then determined. This means that for each individual compound many animals must be injected and processed. While animal testing in vivo is important, it is not the optimal screening system when many compounds have to be examined.

Thus, it would be highly desireable to have an in vitro model of the BBB so as to be able efficiently and inexpensively to screen numerous drugs in a relatively short amount of time. The test system should closely simulate the morphological and physiological characteristics of the in vivo BBB in having tight junctions between cells and similar permeability characteristics, and should be composed of defined cell types.

Another desirable characteristic of an in vitro model is that it should provide a system for testing manipulations of the endothelial cells of a nature as to increase or decrease the passage of drugs from the blood side to the brain side of these cells.

Previous attempts to construct an in vitro model of the BBB have not met the criteria outlined above. Intact brain microvessels (Kumagai, A. K., *J. Biol. Chem.*, 262:15214 (1987)) are likely to contain not only endothelial cells and astrocytes, but mast cells as well. Further, the limited volume and access to the lumen of microvessels precludes their use for vectorial transport studies, and therefore makes them suboptimal as a workable model for the BBB.

Several laboratories claim to have created a BBB in vitro model using brain capillary endothelial cells in the presence of standard growth media (Audus, K. L., et al., *Ann. N.Y. Acad. Sci.*, 507:9 (1987); Van Bree, J. B. B. H., et al., *Pharm. Res.*, 5:369 (1988); Hart, M. N., et al., *J. Neuropath. Exp. Neurol.*, 46:141 (1987)). Cloned bovine brain capillary endothelial cells, grown on a permeable support of glutaraldehyde-treated collagen gel, have been reported to exhibit high transendothelial cell resistance (Rutten, M. J. et al., *Brain Res.*, 425:301 (1987)). However, these studies have demonstrated only one or a few of the inherent morphological, biochemical and functional characteristics of brain capillaries, and the data derived from such systems are often conflicting, in part because in most studies the systems employed incompletely characterized populations of primary cell cultures or cell lines, and in part because the brain capillary endothelial cells were not grown in the proper milieu.

It is known that brain astrocytes influence the properties of brain capillary endothelial cells. Janzer et al. (Janzer, R. C., *Nature*, 325:253 (1987)) disclosed that neonatal rat brain type 1 astrocytes, cultured on filters and transplanted into the eyes of syngeneic animals or chick embryo chorioallantoic membranes, became vascularized by the endogenous endothelial cells, and caused the endothelial cells to exclude the dye, Evans blue.

Exclusion of Evans blue dye or other cationic dyes that bind to albumin is one property of endothelial cells in the brain. These results might be used to predict that astrocytes can cause endothelial cells to exhibit a generally low rate of macromolecular transport. They do not necessarily indicate, however, that the endothelial cells have been induced to form the high resistance tight junctions which are also characteristic of those cells in vivo.

Other in vitro studies have examined the effects of brain astrocytes on ultra-structural properties of endothelial cells. Brain astrocytes enhanced the frequency, length and complexity of tight junctions formed between cultured, brain-derived endothelial cells (Tao-Cheng, J.-H. et al., *J. Neurosci.*, 7:3293 (1987)). Also, fourth passage rat brain capillary endothelial cell cultures, grown in rat brain astrocyte-conditioned medium on endothelial cell matrix-coated substrate, exhibited tight junction biogenesis (Arthur, F. E. et al., *Dev. Brain Research*, 36:155-9 (1987)). Both studies relied solely upon ultrastructural examination of individual groups of treated cells, but neglected to look at resistance of tight junctions.

Thus, an important need still exists for an in vitro model of a BBB that meets all of the criteria necessary for a model to simulate the in vivo situation: 1) a monolayer of endothelial cells essentially all of which are connected by tight junctions; 2) a diffusion barrier for components that do not ordinarily cross the BBB; and 3) a high transendothelial cell electrical resistance barrier indicating the presence of tight junctions that prevent passive diffusion of ions.

SUMMARY OF THE INVENTION

In accordance with the present invention, an in vitro model of the vertebrate BBB is disclosed that simulates important morphological and permeability characteristics of the brain BBB, that permits the efficient and inexpensive screening of CNS drugs, and that allows testing of manipulations of the BBB.

The present invention is based on the effects of the brain microenvironment on the special properties of brain capillary endothelial cells. More specifically, the present invention is based in part upon a reconstruction of interactions between brain astrocytes and brain capillary endothelial cells in in vitro monolayer systems.

This invention is also based on the discovery that treatments that raise effective cyclic AMP concentrations in cultured brain endothelial cells, particularly in conjunction with the presence of components of endothelial cell and brain astrocyte-derived conditioned media or the equivalent, markedly increase the production of tight junctions that exhibit properties of the BBB in vivo such as high electrical resistance, peripheral staining of cells by phalloidin, and a diffusion barrier for substances known ordinarily not to cross the BBB.

This invention is also based upon the discovery that tight junctions between brain microvascular endothelial cells may be disrupted and the blood-brain barrier made more permeable by agents that decrease the effective intracellular concentration of cyclic AMP, interfere with the physiological actions of cyclic AMP, increase the effective intracellular concentration of cyclic GMP, or promote the physiological actions of cyclic GMP, and that such manipulations allow for the facile delivery of drugs across the blood-brain barrier.

It is thus an object of this invention to disclose an in vitro model of the BBB comprising a porous solid support separating monolayer cocultures of microvascular endothelial cells and brain astrocytes juxtaposed in a device that permits physiological interaction between the cell types.

It is another object of this invention to disclose an in vitro model of the BBB comprising a monolayer of microvascular endothelial cells disposed on a filter in contact with conditioned growth media derived from endothelial cells or astrocytes.

It is yet another object of this invention to provide criteria for selecting endothelial cells and astrocytes particularly suitable for the in vitro model.

It is a further object of this invention to provide criteria for selecting substrata for the culture of monolayers of cells in the in vitro model of the invention.

It is still another object of this invention to provide means for elevating the effective intracellular cyclic AMP concentration in microvascular endothelial cells of the in vitro model.

It is yet another object of this invention to provide testing criteria for the genesis of tight junctions in the in vitro model of the invention.

It is yet another object of this invention to provide an in vitro model of a BBB which uses endothelial cells from blood vessels other than brain capillaries.

It is still another object of this invention to provide compositions and methods involving manipulations of cyclic AMP and cyclic GMP levels or physiological effectiveness in order to open up blood-brain barriers in vivo and in vitro and thereby to permit drug delivery across such barriers.

These and other objects of this invention will become clear by reference to the following disclosure and appended claims.

DESCRIPTION OF THE FIGURES

FIGS. 9(A-C), are photographs showing lymphocyte binding and inhibition to binding in brain endothelial cells in culture.

DETAILED DESCRIPTION OF THE INVENTION

Figure 1:
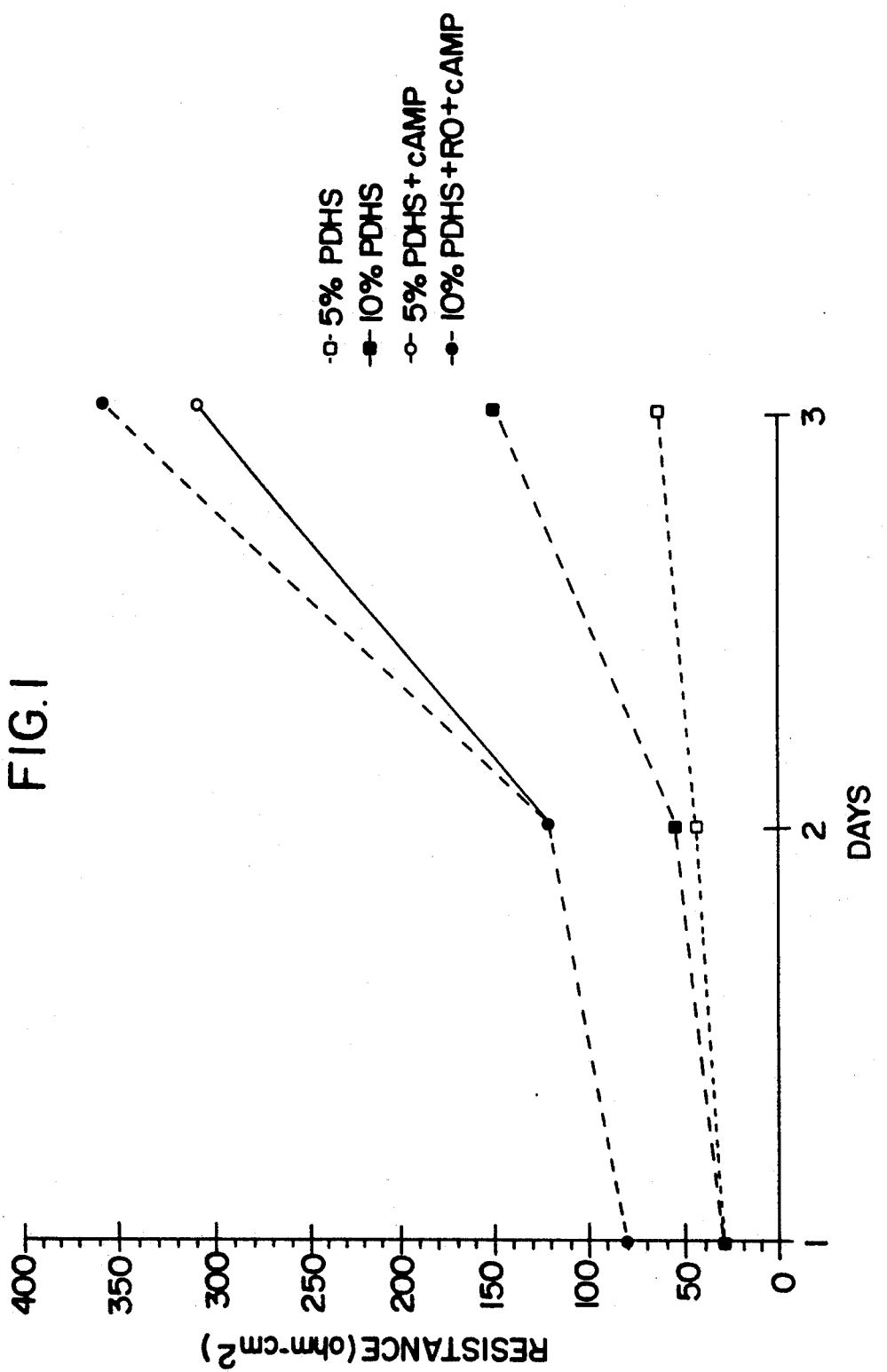
FIG. 1 provides transmonolayer electrical resistance data for the BBB model of the invention using bovine brain capillary endothelial cell cultures.

The present invention comprises an in vitro model of mixed or cloned endothelial cells expressing high electrical resistance tight junctions and other properties of the BBB in vivo.

One embodiment of the invention comprises a chamber separated into at least two compartments by a porous solid support, on one surface of which support is disposed an essentially confluent monolayer of brain microvascular mixed or cloned endothelial cells growing on a particular substratum, the second compartment of the chamber housing an essentially confluent monolayer of brain astrocytes disposed either on a second surface of the chamber or on the underside of the porous solid support, the monolayers of both cell types being in sufficiently close juxtaposition so that products of each cell type can readily reach the cells of the other cell type. By "porous" we mean containing interstices through which water and the solutes contained therein, but not cells, can pass. In an alternative embodiment, the growth medium in contact with the endothelial cells contains, in part, an astrocyte or endothelial cell-derived conditioned medium or equivalent. By "conditioned medium" we mean a tissue culture growth medium into which cultured cells have secreted materials of cellular origin. By "equivalent" we mean cell or tissue extracts containing materials of cellular origin that may in other circumstances be secreted extracellularly. Examples of the preparation of conditioned mediums and equivalents are provided below. In these embodiments of the model, transcellular electrical resistance can be measured directly, as described below. Details as to the construction of these models will be provided below.

In another embodiment of the invention, mixed or cloned microvascular endothelial cells may also be grown on coated microcarrier beads, e.g., Cytodex-3 microcarriers (Pharmacia, Uppsala, Sweden), according to Ryan et al. (Ryan, J., et al., Tissue Cell, 12:619 (1980)). Although in this model transcellular resistance cannot be measured directly, macromolecular transcellular transport, e.g., of labeled albumin, cationized albumin, or glycosylated albumin, and of dyes such as Trypan blue or Evans blue, can be determined (Kempski, O., et al., Acta Neuropathol., 74:329 (1987); Bioadjieva, S., et al., Lab Invest., 50:239 (1984); Smith, R. K., et al., Pharm. Res., 5:466 (1988)). The influence of astrocytes on endothelial cells grown on microcarriers can be determined by first growing brain astrocytes, such as neonatal rat type 1 astrocytes, on the beads, then removing the astrocytes, leaving their extracellular matrix behind. This can be accomplished either by lysing the astrocytes in 5 mM Tris buffer, pH 7.4, containing 1% Triton X-100 for 15 minutes or by incubating the astrocytes in phosphate-buffered saline (PBS) containing 10 mM EDTA for 30 minutes, both solutions containing protease inhibitors, e.g., aprotinin and phenylmethysulfonyl fluoride. Coated beads can be washed 3 times in PBS, then treated with 25 mM NH$_4$OH. After the beads are washed again with PBS, they can be coated with an essentially confluent layer of cultured endothelial cells. Once the endothelial cells reach confluence, they can be maintained in a growth medium containing cultured astrocytes, or in astrocyte-derived or endothelial cell-derived conditioned medium.

In another embodiment, mixed or cloned microvascular endothelial cells can be grown on porous tube-like structures, such as those used in hollow-fiber cell growth devices (Amicon Corp., Danvers, Mass.). Again, a surface of hollow fibers can be coated with astrocytes, from which astrocyte extracellular matrix (ECM) can be prepared as described above. Endothelial cells can then be grown on the astrocyte ECM, and the cells exposed to astrocyte or endothelial cell-derived conditioned medium. In this embodiment, transcellular electrical resistance can be measured by passing current between electrodes inside and outside the hollow fiber. Macromolecular flux can be measured by adding labeled macromolecules outside the fiber, and following their transport across the endothelial cells into the fiber.

Origin of Astrocytes

Purified populations of neonatal rodent brain type 1 astrocytes were prepared according to the procedures of Lillien et al. (Lillien, L. E., et al., Neuron, 1:485 (1988)). In brief, cerebral cortices were removed from neonatal rats, white matter was discarded, and the gray matter mechanically and enzymatically (trypsinization) dissociated. Cells were plated in poly-lysine-coated flasks in Dulbecco's Modified Eagle's Medium (DMEM) plus 10% fetal calf serum (FCS). After 5 days, loosely attached cells were dislodged by shaking, attached cells were passaged into new flasks, and treated with cytosine arabinoside (an anti-mitotic drug) to remove actively proliferating contaminating cells. Finally, astrocytes were maintained in a chemically defined medium and fed twice weekly. Cell type was determined by reactivity with particular sets of antibodies. For example, type 1 astrocytes are fluorescently labeled by an antibody against glial fibrillary acidic protein, but not with the monoclonal antibody A2B5 (which labels type 2 astrocytes) or with an anti-galactocerebroside antibody (which labels oligodendrocytes) (Raff, M. C., et al., J. Neurosci., 3:1289 (1983)).

Origin of Capillary Endothelial Cells

Endothelial cells are prepared from a variety of animal and human sources. For example, mixed populations of endothelial cells may be prepared from purified capillaries derived from rodent and bovine brain, bovine retina, bovine adrenal, bovine aorta, and human omentum or from human umbilical vein. Bovine sources are particularly suitable because of the large amounts of tissue available, the ready availability of fresh tissues, and the similarity of the permeability of bovine capillary cells to that of their human counterparts.

Bovine brain microvascular cells were isolated according to Audus et al., Pharm. Res., 3:51 (1986)).

Briefly, a slurry of brain grey matter in Liebovitz' L-15 medium was homogenized, and the microvascular cell-containing particular fraction was separated on a Dextran cushion. Capillaries were resuspended and homogenized, then passed through a series of nylon filters. Capillaries were digested further with collagenase plus trypsin to provide a population of single mixed endothelial cells. These cells were plated on a collagen or fibronectin treated substratum in 10% plasma-derived horse serum (PDHS) in Dulbecco's modified Eagle's Medium (DMEM). Rat brain microvascular endothelial cells were prepared similarly according to Bowman, et al. (Bowman, P. D., et al., In Vitro, 17:353 (1981)). Briefly, brain grey matter is minced and digested with collagenase and dispase. The particulate matter is separated over a 25% bovine serum albumin (BSA) cushion, and the pellet further digested with collagenase and DNase. Finally, endothelial cells are isolated on a Percoll gradient, and washed cells are plated on a collagen-treated substratum in DMEM+20% plasma-derived horse serum (PDHS)+150 µg/ml endothelial cell growth supplement (ECGS, available from Sigma Chemical Co., St. Louis, Mo.); (McGuire, P. G., et al., Lab. Invest., 57:94 (1987)).

To prepare mixed bovine aortic endothelial cells, aortas were trimmed of adventitia and connective tissue, cut open to expose the intimal layer, and the internal aspect contacted with 0.1% collagenase in RPMI 1640. After incubation for 20 minutes at 37° C., the loosened cells were scraped into DMEM+10% fetal calf serum (FCS) and plated into tissue culture flasks. For rodent aortic endothelial cells, the exposed intima were placed on a collagen-treated surface in a minimal quantity of growth medium (DMEM+20% FCS+150 µg/ml ECGS); endothelial cells will grow out from the explant and proliferate in this growth medium.

Mixed populations of human endothelial cells may also be isolated from fresh umbilical veins. After cannulating the vein and flushing it with RPMI 1640 medium, the intimal layer is exposed to 1 mg/ml collagenase in RPMI 1640. After 15 minutes at about 37° C., the detached cells are washed out of the vein, pelleted by centrifugation, the cell pellet suspended in DMEM+20% FCS, and the cells plated on a collagen-treated substratum (Gimbrone, M. A., et al., J. Cell Biol., 60:623 (1974)). These cells are also available commercially (Clonetics, San Diego, Calif.).

Cells are identified as endothelial by immunofluorescence assay with anti-von Willebrand protein (rabbit serum from Bering Diagnostics, La Jolla, Calif.) and uptake of di-I-labeled acetylated LDL (Molecular Probes, Junction City, Oreg.). Endothelial cells are typically passaged once a week and maintained in DMEM+10% or 20% FCS or 10% PDHS.

Endothelial cell cultures can be cloned, if desired, using the cloning ring technique. Cells are plated in at low density (1000 cells per 10 cm plate) in 10% FCS. Plastic cloning rings, dipped in silicone grease, are paced on cells so as to encircle and isolate single or paired cells on an inverted microscope. Once the clone expands, the cells are detached by trypsinization within the ring and transferred to a well of a multi-well culture disk. Multiple clones of microvascular endothelial cells from bovine brain, bovine aorta, rat aorta, and rat brain can be isolated by this technique.

Astrocyte-Derived Conditioned Medium

Neonatal rat brain type 1 astrocytes were grown to confluency in poly-D-lysine-coated 75 $cm^2$ flasks. Fresh medium was added to the cells, and removed after 2-4 days. The medium was filtered through a 0.2µ Millipore filter, and stored frozen at −80° C. in small aliquots.

Endothelial Cell-Derived Conditioned Medium

Bovine aortic or retinal endothelial cells were grown to confluency in 75 $cm^2$ flasks. Fresh medium was added to the cells, and conditioned medium collected and stored as above.

Astrocyte Extract

Type 1 astrocytes from neonatal rat brain were grown as above. Cells were scraped from the dish in 3 ml of ice-cold DMEM, and homogenized in a Dounce homogenizer at ice-bath temperatures. After centrifuging the homogenate at 40,000 rpm for 30 minutes in a Beckman Instruments SW40 rotor, the supernatant fluid was filtered through a 0.2µ Millipore filter, and small aliquots stored frozen at −80° C.

Brain Extract

Neonatal rat brain cortex was removed and homogenized in DMEM (3 ml per gm. tissue, wet wt.) in a Dounce homogenizer. The homogenate was centrifuged and processed as for the astrocyte extract above.

Elevation of Cyclic AMP Concentrations

Cultures of endothelial cells were treated with one or more agents known to increase cyclic AMP concentrations. These include, but are not limited to: 1) from about 10 to about 100 µM of a β-adrenergic agent, such as isoproterenol, that binds to specific β-adrenergic receptors on cell surfaces and stimulates G-protein-mediated activation of adenylate cyclase; 2) serotonergic compounds such as 5-hydroxytryptamine; 3) forskolin, (Sigma Chem. Co., St. Louis, Mo.) an agent that directly activates adenylate cyclase; 4) parathyroid hormone; and 5) calcitonin gene related peptide. Adding an inhibitor of cyclic AMP phosphodiesterase, the enzyme that degrades cyclic AMP to adenylic acid, will accentuate the cyclic AMP elevating effects of the aforementioned modalities; examples of such inhibitors are 4-(3-butoxy-4-methoxybenzyl)-2-imidazolidinone (Hoffman-LaRoche, Nutley, N.J.), theophylline and methylisobutylxanthine (Sigma Chem. Co.), Rolipram (Berlex, Inc.) and RO-20-1724 (BioMol, Inc., Phymouth Meeting, Pa.). In addition, certain derivatives of cyclic AMP can be used to elevate the effective cyclic AMP concentration in such cells; such derivatives include 8-bromo cyclic AMP (Sigma Chem. Co) and 8-(4-chlorophenylthio)cyclic AMP (Boehringer-Mannheim Corp., Indianapolis, Ind.). By "effective cyclic AMP" we mean endogenous cyclic AMP or cyclic AMP derivatives to which endothelial cells are permeable and which act physiologically as does endogenous cyclic AMP within such cells. By "effective cyclic GMP" we mean endogenous cyclic GMP or cyclic GMP derivatives to which endothelial cells are permeable and which act as does endogenous cyclic GMP within such cells. By "physiological action" of cyclic AMP or cyclic GMP or derivatives thereof we mean those immediate biochemical reactions of these cyclic nucleotides that lead ultimately to the physiological actions ascribed to them. For example, cyclic AMP activates certain protein kinases that catalyze the phosphorylation of hydroxyamino acid residues such as serine, threonine and tyrosine in particular proteins, such phosphorylation activating these proteins. Effects of cyclic AMP are reversed by phosphoprotein phosphatases that catalyze the de-phosphorylation of the aforementioned hydroxyamino acid residue-containing proteins.

When brain capillary endothelial cells were grown on a porous solid support with a growth medium containing PDHS plus one or more of the aforementioned agents that elevated the actual or effective intracellular cyclic AMP concentration, transmonolayer electrical resistance increased about 7-fold, from about 50 to about 350 ohm-cm$^2$ (FIG. 1). However, when in this system, bovine aortic endothelial cell-derived conditioned medium (BAEC-CM) was also present, the transmonolayer electrical resistance increased about 10-fold (Example 5). Growing endothelial cell monolayers on astrocyte extracellular matrix potentiated the effects of cyclic AMP and BAEC-CM, producing as much as a 26-fold increase in resistance (Example 5). Thus, the BBB model of this invention is capable of providing transmonolayer electrical resistances of at least 200 ohm-cm$^2$, preferably greater than about 300 ohm-cm$^2$, more preferably greater than about 1000 ohm-cm$^2$ up to about 1500-2000 ohm-cm$^2$.

In addition, it has been discovered that an elevation of actual or effective cyclic AMP concentrations, with consequent formation of tight junctions between mixed endothelial cells as determined by electrical resistance measurements, was also associated with substantial peripheral staining by phalloidin, a toxin produced by Amanita phalloides that is known to bind to filamentous actin and prevent their depolymerization (Stryer, L., "Biochemistry", 3d., W. H. Freeman, N.Y. 1988, p. 940). The belt-like pattern of phalloidin staining in these treated endothelial cells is similar to that seen in epithelial cells exhibiting high resistance tight junctions. (Gumbiner, B., J. Cell Biol., 107:1575 (1985).) In addition, when endothelial cells were grown with endothelial cell-derived or astrocyte-derived conditioned medium plus cyclic AMP enhancing agents such that peripheral phalloidin staining of cells was substantially present, transmonolayer electrical resistance was increased over that obtained in the absence of conditioned medium.

It has also been discovered that the formation of tight junctions between endothelial cells in the blood-brain barrier model of the invention is substantially enhanced when endothelial cells are grown from the time of their isolation in the presence of astrocyte-derived conditioned medium (ADCM). Thus, when endothelial cells are passaged onto filters, e.g., Costar filters, they are preferably grown in a medium containing 50% ADCM made in MEM with 10% fetal calf serum and 50% N2 (a chemically-defined medium). After 2-3 days of growth on the filters, they may be treated with a cyclic AMP analogue and a cyclic AMP phosphodiesterase inhibitor (e.g., Rolipram or RO 20-1724).

In addition, it has been discovered that, when endothelial cells are cultured in concentrations of fetal calf serum substantially lower (e.g., 0.5% to 5%) than the customary 10% used for culturing such cells for other purposes, increased cellular resistivity in the bloodbrain model of the invention may be attained.

Decreased Cyclic AMP Concentrations or Physiological Activity

As noted above, increases in cyclic AMP in tissues by whatever means (e.g., addition of cyclic AMP analogues, addition of compounds that stimulate endogenous adenylate cyclase activity, or addition of compounds that inhibit the activity of cyclic AMP phosphodiesterase thereby inhibiting cyclic AMP degradation) result in enhanced tight junction formation between brain endothelial cells.

It has also been discovered that removal of cyclic AMP analogues or other agents that elevate cyclic AMP levels from endothelial cell cultures in the bloodbrain model of the invention produces a rapid decrease in resistance, signalling increased permeability of tight junctions.

These discoveries have led to other approaches to regulating tight junctions between brain endothelial cells: (a) compounds that inhibit formation of endogenous cyclic AMP by adenylate cyclase; (b) competitive inhibitors of cyclic AMP; (c) inhibitors of protein kinases, the enzymes that are activated by cyclic AMP; and (d) stimulators of protein phosphatases, the enzymes that dephosphorylate proteins that had been phosphorylated, and thereby activated, by the cyclic AMP system.

The basis of approach (a) above is as follows. A system for the regulation of adenylate cyclase activity in plasma membranes consists of GTP; a $G_i$ regulator protein which, when bound to GTP, inhibits the activity of adenylate cyclase; a $G_s$ regulatory protein which, when bound to GTP, activates adenylate cyclase; and, agonists that increase the binding of GTP to $G_i$ or $G_s$. It has now been discovered that agonists that increase the binding of GTP to $G_i$, such as α-adrenergic agents and adenosine A1 receptor agonists [e.g., cyclopentyladenosine (CPA) and the (−) stereoisomer of $N^6$-(phenylisopropyl)-adenosine (R-PIA)], particularly the latter agonists, are effective in reducing the resistance of brain endothelial cells. Such observations may be made in vitro in the blood-brain model of the invention or in vivo in brain infusion and behavorial test systems in mice, as shown in the in vivo examples below. For example, it was found that $G_i$ agonists that presumably inhibited the cellular production of cyclic AMP lowered the amount of morphine that had to be administered intravenously to mice in order to produce analgesia (morphine does not penetrate well into the brain). Another in vivo test system comprises the intravenous administration of a test drug to an unanesthetized animal, the injectate also containing labeled tracer substances that normally do not penetrate the BBB. Thereafter, the test animal is injected with an anesthetic, followed by phosphate-buffered saline and a tissue fixative. The brain is then removed and dissected, and the amount of tracer substance quantified. Observation with these test systems suggest that agents that inhibit adenylate cyclase and reduce cyclic AMP production increase the permeability of tight junctions and open up the blood-brain barrier, thereby providing a drug delivery system.

Approach (a) above also includes the use of inhibitors that block the binding to the receptors for the aforementioned Gs system of endogenous ligands, e.g., norepinepurine, that stimulate the $G_s$ system. By this means, endogenous production of cyclic AMP is reduced, thereby reducing tight junction formation between brain microvascular endothelial cells. Approach (a) also includes agents that directly inhibit adenylate cyclase, such as the synthetic nucleoside dideoxyadenosine.

The basis of approach (b) above is that competitive inhibitors of the action of cyclic AMP will increase the permeability of tight junctions, thereby opening up the blood-brain barrier. Compounds of this type that can be tested in the blood-brain model of the invention include the $R_p$ diastereoisomer of cyclic AMP.

The basis of approach (c) above is as follows. Cyclic AMP is known to act physiologically by activating one or more protein kinases that, in turn, catalyze the phosphorylation of key proteins. Thus, inhibitors of protein kinases should nullify the effects of cyclic AMP on tight junction formation between brain endothelial cells. As will be detailed in the examples below, protein kinase inhibitors such as K252a and staurosporine at nM (10–200 nM) concentrations can markedly reduce the resistance of brain endothelial cell cultures. Both inhibitors were reversible. At the light microscope level, it was discovered that either removing cyclic AMP or adding a protein kinase inhibitor caused clear separations of endothelial cell tight junctions.

The basis of approach (d) above is that dephosphorylation of those key proteins whose phosphorylation had been catalyzed by cyclic AMP-activated protein kinases will produce an unphosphorylated protein that is inactive in maintaining tight junctions among endothelial cells.

Increased Cyclic GMP Concentrations or Activity

Cyclic GMP, another regulatory cyclic nucleotide, is produced from GTP by the enzyme guanylate cyclase.

It has now been discovered that increasing cyclic GMP concentrations or physiological activity in brain endothelial cells leads to a decrease in resistance, and thus to an increase in tight junction permeability. Increased concentrations or physiological activity of brain endothelial cell cyclic GMP can be achieved by, for example, 8-bromo-cyclic GMP, atrial natriuretic factor and sodium nitroprusside, and by cyclic GMP phosphodiesterase inhibitors such as dipyridamole (Research Biochemicals, Inc.) or Zaprinast (Rhone-Poulenc). It was observed, for example, that nitroprusside at concentrations of from 0.1 to 100 $\mu M$ markedly inhibited the effect of a cyclic AMP analogue, RO-20-1724, on elevating the resistance of brain endothelial cells in the blood-brain model of the invention. Such agents may be used in the aforementioned in vivo test systems to determine their effect on the opening up the blood brain barrier in test animals. For example, the in vivo morphine analgesia test system described below can be used to demonstrate that sodium nitroprusside opened up the blood-brain barrier to morphine, and that dipyridamole opened up the blood-brain barrier to enkephalin, an endogenous opiate in vertebrates that does not penetrate significantly into the brain when administered in the peripheral circulation.

Construction of a Chamber BBB Model

In a general embodiment of this invention, brain capillary endothelial cells are grown on a porous substratum-coated solid support, e.g., filters or membranes. It has been found that endothelial cells can attach to and grow on Nucleopore polycarbonate filters (Costar, Inc., Cambridge, Mass.), Millicell CM and HA porous nitrocellulose filters (Millipore Corp, Bedford, Mass.), and collagen membranes (ICN Biomedical, Inc., Costa Mesa, Calif.). The Millicell CM and Nucleopore polycarbonate filters required pre-treatment, i.e., coating, with extracellular matrix material (ECM, see below), components in order to promote adhesion of cells to the filter. Nucleopore filters promote media exchange across the filter, and permit cellular processes to cross through. Filters allow cells more completely to establish blood side and brain side domains, as they permit separate manipulation of the two compartments of the chamber.

Porous solid supports can be coated with ECM by soaking them in an aqueous solution of laminin, vitronectin, or fibronectin (typically, from about 10 to about 50 $\mu g/ml$), Matrigel® (an extract of EHS sarcoma obtainable from Collaborative Res., Bedford, Mass.) in PBS, type I rat tail collagen or type IV collagen in dilute acetic acid (Collaborative Research, Inc., Collagen Corp, and New York Blood Bank, N.Y.), or astrocyte extracellular matrix (AECM).

In a preferred embodiment, filters were coated with astrocyte extracellular matrix (AECM) synthesized by astrocytes, in the following manner. Rat brain type I astrocytes, produced as described above, were grown on filters in a chemically-defined medium. Once cells reached confluence, they were lysed by a low ionic strength buffer containing a nonionic detergent, e.g., Triton X-100, and rinsed with PBS containing a protease inhibitor such as aprotinin. This removed the cells and left behind AECM as a coating on the filter. Alternatively, AECM was generated by solubilizing the cells of a confluent monolayer of astrocytes with nonionic detergent, and then extracting residual extracellular matrix components with a denaturant such as 6M urea, 6M guanidine HCl or 2M $MgCl_2$. This extract was dialyzed against physiological saline before adding to endothelial cells being cultured on filters or used as a filter coat prior to adding endothelial cells.

In one embodiment of the chamber-type in vitro model of the BBB of this invention, an essentially confluent monolayer of rat brain type 1 astrocytes was disposed on one side of a porous solid support, and an essentially confluent monolayer of endothelial cells was disposed atop an ECM coating on the opposite side of the porous solid support. The thus-obtained co-culture device was then affixed in a chamber, effectively dividing the chamber into at least two compartments, one of which represents the brain side (endothelial cell side) and the other the blood side of a BBB. The cells were then placed in contact with a growth medium, preferably containing PDHS.

In another embodiment, an ECM-coated porous solid support was affixed in a chamber. On one ECM-coated surface of the porous solid support there was disposed a culture of astrocytes; endothelial cells were then plated at low density (about $10^5$ cells/30 mm filter) onto the opposite ECM-coated surface. The astrocytes "condition" the growth medium that contacts the endothelial cells and may induce appropriate differentiative changes in the endothelial cells, including formation of tight junctions. The cells were grown in a culture medium containing serum, preferably PDHS.

In another embodiment, microvascular endothelial cells were disposed on an uncoated or EMC-coated porous solid support as described above, and the support was affixed in a chamber, on a surface of which there was disposed a culture of brain astrocytes. The growth medium must contact both the endothelial cells and astrocytes to effect biochemical interaction between the co-cultures.

In yet another embodiment, microvascular endothelial cells were disposed on an ECM-coated porous solid support as described above, but astrocytes were absent from either the contralateral side of the porous solid support or from a surface of the chamber. Instead, the growth medium in the blood compartment of the chamber, i.e., the compartment opposite that which houses endothelial cells, was supplemented with from 0% to 100% with astrocyte-derived or endothelial cell-derived conditioned media, or with brain or other tissue extracts, obtained as described above, as required.

Agents that are intended to elevate intracellular concentrations of cyclic AMP in endothelial cells or to increase the concentration of effective cyclic AMP may be added to the growth medium, as can be dyes, e.g., trypan blue or Evans blue, or other macromolecules that are used to test for tight junction resistance.

It is preferred that the glucose concentration of a growth medium in contact with endothelial cells not be higher than physiological in vertebrates, i.e., approximately 100 mg/dl.

Assay for Tight Junctions

The presence of tight junctions in the endothelial layer of the BBB model can be detected using reagents that recognize proteins associated with tight junctions. For example, the monoclonal antibody 40.76, made against ZO-1 tight junction protein, specifically recognizes an antigen on both bovine and mouse endothelial cells (Anderson, J .M. et al., *J. Cell Biol.*, 106:1141 (1988); Stevenson, R. B., et al., *J. Cell Biol.*, 103:755 (1986)). This approach allows the user to detect the formation of tight junctions among small subsets of endothelial cells, and to refine culture conditions to enhance the formation of tight junctions.

The degree of tightness of tight junctions can be also assessed by transcellular electrical resistance measurements. For transendothelial cell resistance measurements, cells were grown on a porous solid support, e.g., a filter or membrane attached to a holding device in order adequately to suspend the cellular monolayer, such as the Costar Transwell apparatus or the ICN Cellogen. Transmonolayer resistance is measured, for example, with the device of Perkins et al. (Perkins, F. M., et al., *Am. J. Physiol.*, 241:C154 (1981)). Cells were maintained in a growth medium or physiological saline, and calomel electrodes on each of the endothelial cells are connected by a saturated KCl - 3% agar bridge. Current is passed between two Ag—AgCl electrodes and the voltage measured with a Keithly multimeter. Resistance is calculated from the change in voltage across the monolayer induced when a short current pulse (10–100 μamp) is applied. The resistance of the filter or membrane alone is subtracted. The resistance, multiplied by the surface area of the filter or membrane, yields the resistance in ohms-cm$^2$.

As noted above, peripheral binding of the toxin phalloidin reveals the presence of belt-like filamentous actin, a hallmark of tight junction formation among endothelial cells. Staining of filamentous actin by phalloidin can be visualized using derivatives such as phalloidin coumarin phenylisothiocyanate or fluorescent FITC-phalloidin or TRITC-phalloidin (Signma Chem. Co., St. Louis, Mo.).

Another means for assessing the formation of tight junctions among endothelial cells is to determine the transport of macromolecules from the apical blood side to the abluminal brain side. For example, the water-soluble dye Evans blue (mol. wt. 960) that binds strongly to albumin (Freedman, F. B., et al., *Am. J. Physiol.*, 216:675 (1969)), can be used to assess the tightness of newly formed endothelial cell junctions; tissues with tight junctions that exclude the dye or exhibit limited transport will remain white, whereas those without tight junctions or that exhibit significant transport capabilities will be stained blue as the dye passes through the junctions. Other water-soluble, macromolecular markers for tight junction formation include fluorescein isothiocyanate bound to dextran (FITC-dextran. mol. wt. 20,000, Sigma Chem. Co.) and $^{125}$I-labeled albumin (DuPont/NEN, Wilmington, Del.). Fluorescent dextrans of other sizes and sodium fluorescein itself may be used as well.

Still another means for assessing the tightness of junctions among endothelial cells in the blood-brain model of the invention is to compare the transport of a hydrophilic compound, e.g., sucrose, and a hydrophobic compound of similar size, e.g., chlorambucil, across filters with and without monolayered endothelial cells. When the transmonoloayer resistance is high, the transport of sucrose should be low compared to that of chlorambucil (or other hydrophobic compounds of similar size). Alternatively, when the resistance is high, the transport of sucrose should be much less (e.g., 50-fold or more) than across cell-free filters. Contrariwise, in "leaky" cell junctions, the relative transport of sucrose will be substantially increased.

Assessment of Ligand Binding, Transcytosis and Drug Delivery

The access in the model of the invention to both sides of a differentiated endothelium or ECM-coated porous solid supports permits the assay of specific binding and uptake of radiolabeled ligands from an apical (luminal) or basolateral (abluminal) aspect. Furthermore, by adding a labeled probe to one side of the porous solid support, one can assess the ability of the probe to be transcytosed from one side of the monolayer to the other.

The model also allows for testing the access of potential new therapeutics to the brain parenchyma. For example, drugs such as L-DOPA can cross the BBB, being recognized and transported by amino acid transporters. Lipophilic drugs are also able to penetrate the BBB. However, as indicated above, potentially therapeutic drugs that are not lipophilic and for which no specific transport mechanism exists may be unable to penetrate the BBB or may do so at rates insufficient to maintain a therapeutic drug level in the brain. The in vitro model of the BBB of this invention can also be used to test tight junction-disrupting compositions. It has been found by immunohistological methods that a molecule immunologically related to the mouse cell-adhesion molecule E-cadherin is present on mouse endothelial cells. The expression of the E-cadherin-like molecule is enhanced in cultures of brain endothelial cells exhibiting increased resistance (Example 9).

Vasogenic Brain Edema

It is generally thought that brain edema is caused by increased tight junction permeability (decreased resistance) and/or increased pinocytosis. To the extent to which enhanced tight junction is important, agents that increase cyclic AMP concentration or physiological activity in brain microvascular endothelial cells may be of therapeutic value. These include cyclic AMP analogues, agonists that bind to receptors coupled to the Gs regulatory protein, adenylate cyclase activators, cyclic AMP-specific phosphodiesterase inhibitors, protein phosphatase inhibitors, and protein kinase stimulators. We have discovered, in this connection, that the phosphodiesterase primarily responsible for degrading cyclic AMP in brain microvascular endothelial cells is a member of the class termed the Type III cyclic GMP-noninhibitable phosphodiesterase, and that this enzyme is inhibited by compounds such as Rolipram and RO-20-1724 mentioned above.

Other Uses of the Model

While the foregoing illustrates preferred modes of practicing this invention, other embodiments of the basic concepts of the present invention can also be practiced. For example, the model can be used with cocultures of pulmonary or aortic arterial endothelial cells, with other cells of vascular walls, e.g., smooth muscle cells, in order to study morphological and metabolic interactions between the two types of cells, as well as transcellular transport and drug permeability. The model may also be used as a chemotaxis chamber to study brain migration of lymphocytic cells through monolayers of brain endothelial cells to analyze CNS diseases such as multiple sclerosis. Yet another use of the model is to test other endothelial cell barriers, such as in the testes and retina. Still another use of this model is to screen reagents useful to prevent or ameliorate brain inflammation, such as in the embodiment described below wherein the model is used to screen compositions for the modulation of the adhesion of white blood cells to brain endothelia.

MODULATION OF LEUKOCYTE ADHESION TO BRAIN ENDOTHELIAL CELLS

The present blood brain barrier model was also used to screen reagents useful to prevent or ameliorate brain inflammation. The blood brain barrier model was used to select reagents that prevent the attachment of inflammatory white blood cells to the brain endothelium. This model, in conjunction with analysis of brain tissue, allowed identification of one of the receptors that white blood cells use to adhere to brain endothelial cells. Once this receptor was identified, reagents and methods useful for ameliorating or preventing inflammation were ascertained, as were therapeutic compositions useful for treating brain-inflammatory disease such as multiple sclerosis.

White blood cells (leukocytes) travel continuously in the general circulation. At the site of an injury or other inflammatory stimulus, cells that line blood vessels (endothelial cells) become activated to express molecules that are adhesive for leukocytes. Thus, following an inflammatory stimulus, leukocytes bind to the activated endothelium. Once bound, the leukocytes migrate across the blood vessel wall to enter the injured site and release toxic mediators to combat infection. Unfortunately, the leukocyte toxins can also cause indiscriminate tissue damage. Such is the case with multiple sclerosis (MS). In MS, large numbers of leukocytes leave the blood stream within the brain and cause extensive tissue damage. See Hickey, W. F., Psychneuroimmunology II, Academic Press (1990).

In order for leukocytes to enter any tissue, they must first bind to the vascular endothelium. It has been shown in other disease systems that, in spite of the initial insult, if leukocyte binding to the endothelium at the damaged site is inhibited, then the leukocytes do not enter the tissue and further damage is greatly avoided. Simpson et al., *J.Clin.Invest.* 81: 624–629 (1988) disclose that the administration of a monoclonal antibody that binds to a leukocyte cell adhesion-promoting glycoprotein (Mo1; CD11b/CD18) resulted in reduced injury to heart tissue because fewer leukocytes (neutrophils) bound to the heart tissue.

The mechanics of leukocyte adhesion to endothelial cells involves, in part, the binding of cell surface receptors on leukocytes to the corresponding cell surface receptors on endothelia. Both leukocytes and endothelial cells are known to express various adhesion-promoting receptors at various times in response to various stimuli. For reviews of adhesion receptors of the immune system, see generally, Springer, *Nature* 346: 425-434 (1990), and Osborn, *Cell* 62: 3-6 (1990) both of which are herein incorporated by reference. The expression of cell adhesion molecules is not predictable, and may vary widely in response to different inflammatory stimuli and in different anatomical locations. For example, Tuomanen et al., *J. Exp. Med.* 170: 959–968 (1989) show that antibodies directed against the CD18 family of adhesion-promoting receptors blocks the migration of leukocytes across the blood brain barrier in response to acute inflammatory stimulus of bacterial origin. Anti-CD18 was shown to not block leukocyte migration to the lung. Vedder et al., *Surgery* 106: 509 (1989).

Circulating leukocytes may express the VLA-4 receptor, and this has been show to bind to the VCAM-1 receptor on cytokine-activated human endothelial cells. Elices, et al., *Cell* 60: 577–584 (1990). The different types of molecules induced on blood brain barrier endothelial cells during brain inflammation, and the role that they play in chronic inflammatory brain disease, such as MS, is poorly understood.

A. Ameliorating or Preventing Brain Inflammation

The present embodiment was directed toward finding reagents that modulate leukocyte adhesion in the brain. The blood brain barrier model of the present invention was one system used. Using this model, brain endothelial cell samples, prepared in accordance with the present description, were activated with inflammation mediators. To a panel of these activated cell samples, leukocytes were introduced in the presence of a different putative receptor-blocker for each sample. Individual samples were assayed for the presence or degree of leukocyte adhesion. Here, among the various reagents tested, two antibodies directed against VLA-4 (the leukocyte cell adhesion molecule) were shown to block lymphocyte binding to brain endothelium.

A separate assay produced the same results. Essentially, slices of brain tissue were analyzed for their ability to bind leukocytes in the presence of putative cell adhesion modulators. In this system, another novel aspect of the present invention was developed. Rats were injected with human tumor cells in order to induce inflammation in the brain. Previously, it was not known that this method could induce traffic across the blood brain barrier into the brain. Further, the type of inflammation induced is very much like that seen in multiple sclerosis victims where inflammation is characterized by small vessels, with activated almost cuboidal endothelium. The vessels appear very similar to the "high endothelial venules" seen in lymphoid tissues. Further, the vessels are surrounded by a cusp of lymphocytes, and active lymphocyte traffic is apparent. While MS-type inflammation has been observed, it has never before been induced by this method. Thus, induction of brain inflammation using tumor cells possesses great utility in obtaining tissue for an in vitro model of multiple sclerosis.

After an appropriate length of time, rat brains in which inflammation had been induced were removed and sectioned. To these sections, leukocytes were added, in the presence of the putative cell adhesion modulator to be screened. Here too it was found that the anti-VLA-4 antibodies inhibited leukocyte adhesion.

Figure 8A:
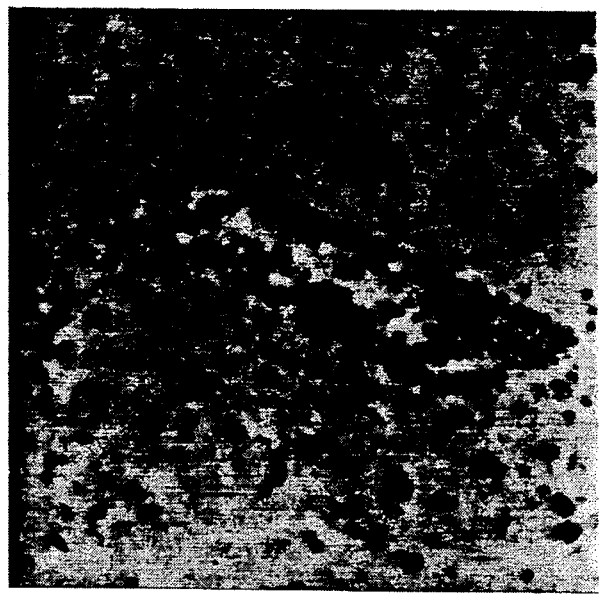
FIGS. 8(A and B), are photomicrographs of sections from a brain sections in which MS-type inflammation was induced via intracranial injection of human tumor cells. Human and mouse lymphocytes were allowed to contact the sections, and, as seen in FIG. 8(A), bind selectively to exposed brain endothelium.
In FIG. 8(B), the lymphocytes were treated with an antibody that inhibits the human VLA-4 receptor (anti-human $\beta$-1 integrin) and as can be seen, the human lymphocyte (large cell) binding is substantially inhibited.
Figure 8B:
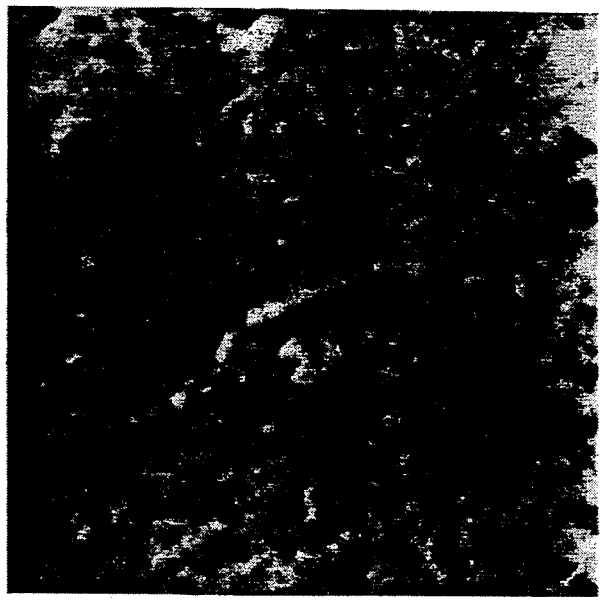
Figure 9C:
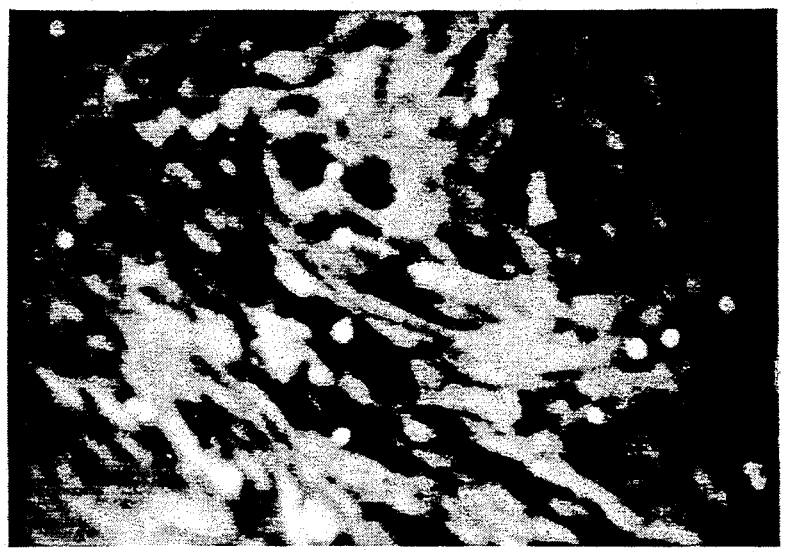
In FIG. 9(C), the lymphocytes were pretreated with anti-human $\beta$-1 integrin monoclonal antibody, and their binding to the stimulated endothelium is substantially inhibited.
Figure 9B:
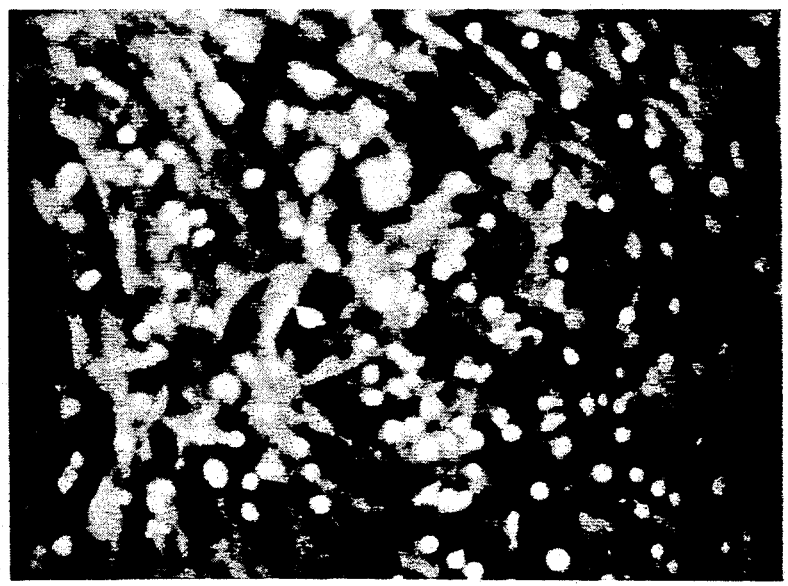
In FIG. 9(B), the endothelium has been treated with an inflammatory reagent, and lymphocyte binding is increased substantially.
Figure 9A:
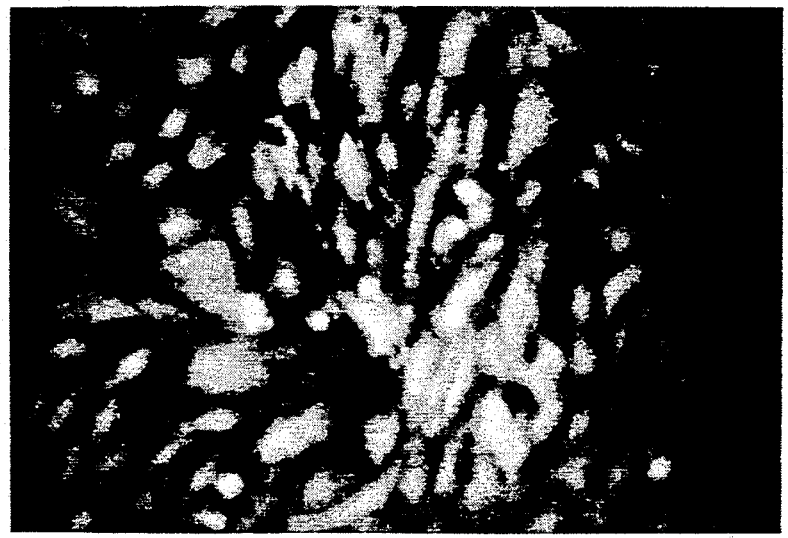
FIG. 9(A) shows the low level binding of lymphocytes to the BBB model endothelium.
Figure 10:
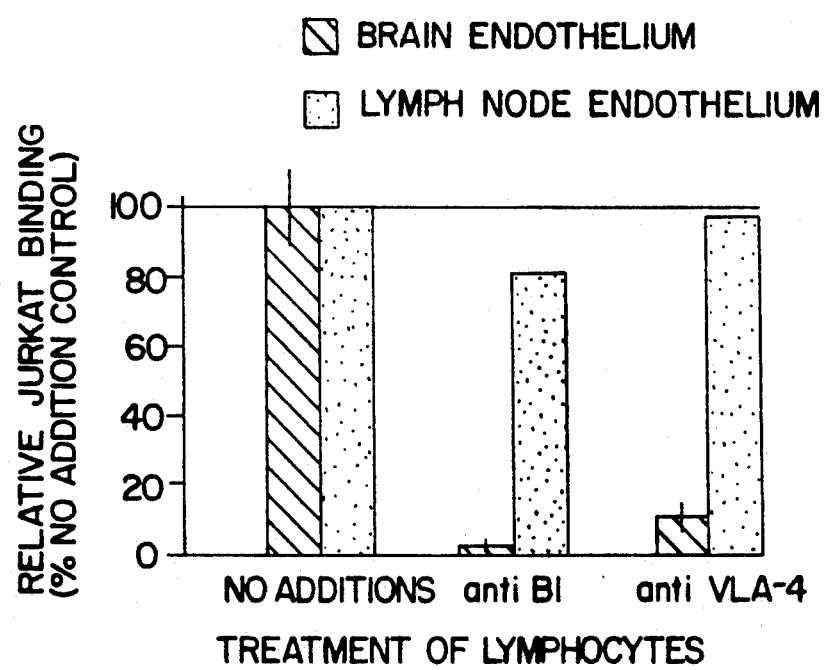
FIG. 10 is a graph showing the relative degree of lymphocyte binding to blood vessels in sections of inflamed brain tissue, and, as a basis for comparison, normal lymph node tissue. The "no additions" column shows brain tissue (scored) and lymph node endothelium (solid) to which untreated lymphocytes have been added. The degree of binding is represented as 100%. In the next two columns, lymphocytes have been pretreated with anti-VLA-4 reagents. The middle bars show lymphocytes pretreated with anti-β-1 monoclonal antibody, the right-hand bars show lymphocytes pretreated with anti-α-4 monoclonal antibody. In both cases, lymphocyte binding in brain tissue is almost completely inhibited, as compared to the control. But, lymphocyte binding to lymph node endothelium, in both cases, is not significantly inhibited.
Figure 11:
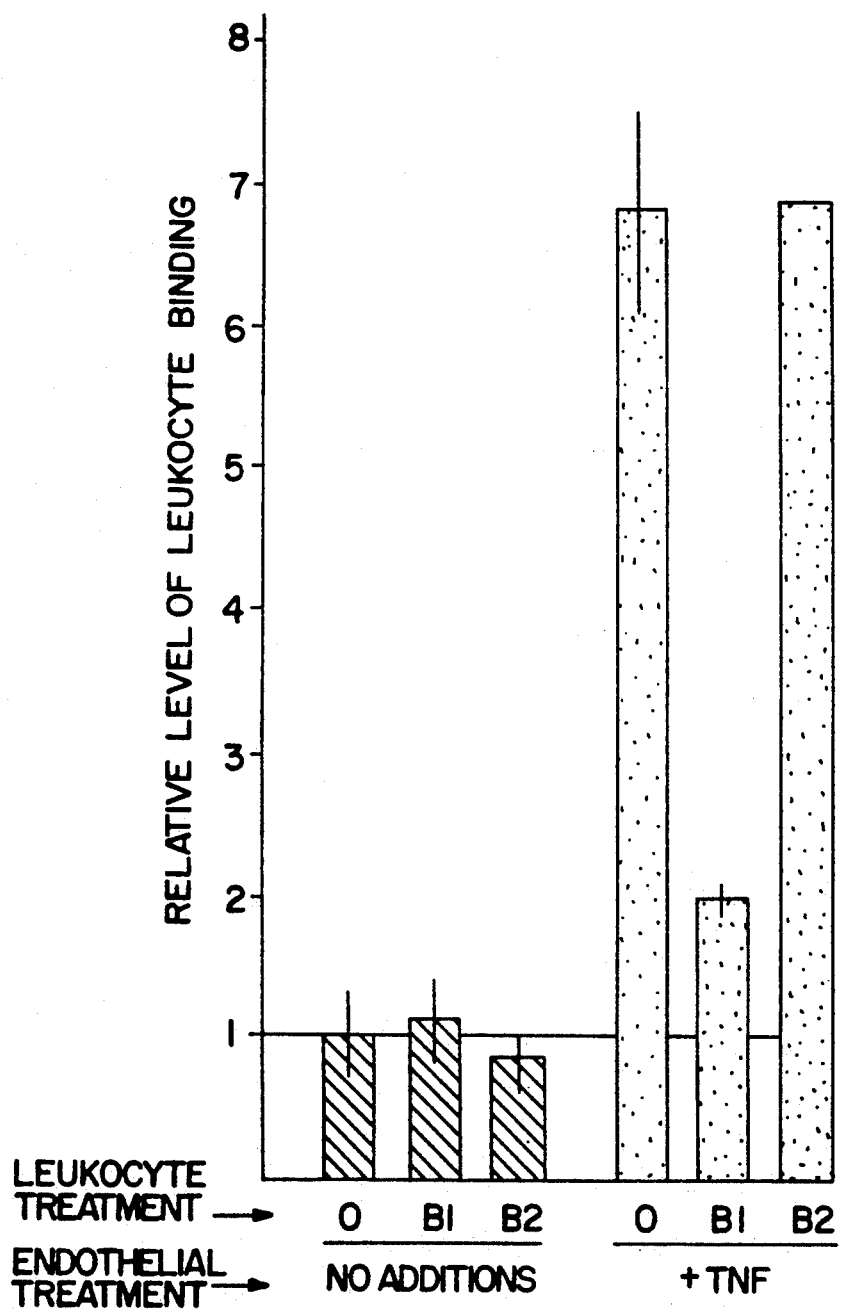
FIG. 11 is a graph showing the relative degree of Jurkat T-cell lymphocyte binding to brain endothelial cells in the BBB system. As can easily be seen, the anti-β-1 antibody effectively inhibited the binding of leukocytes to TNF-α activated brain endothelial cells. Anti-β-2, as a control, on the other hand, approaches the untreated control. Plainly, the β-1 subunit provides an effective target for preventing VLA-4/VCAM-1 interaction in the brain.

This inhibition is graphically illustrated in the Figures. FIG. 8, Panel A shows a brain section in which no antibody is added. The small dark dots are leukocytes against the background of inflamed brain endothelial cells. As can be seen, the leukocytes are quite densely bound to the vessels in inflamed tissue. FIG. 8, Panel B shows inhibition of binding by antibodies directed against the $\beta 1$ subunit of VLA-4. FIG. 9 shows a brain endothelial culture to which lymphocytes have bound. Panel A illustrates binding to unstimulated endothelium. Panel B shows binding to endothelium stimulated for twelve hours by TNF$\alpha$. In Panel C, the lymphocytes have been pretreated with anti-$\beta$-1 integrin and their binding to stimulated endothelium is greatly inhibited. As described in Example 21, below, the binding density of human leukocytes to brain sections was confirmed by using an internal population of mouse leukocytes, a population not recognized by the anti-human reagent. This quantification confirmed the visual observation that anti-VLA antibodies prevented leukocyte binding to brain sections in which multiple sclerotic-type inflammation had been induced. (FIG. 10). Further, leukocyte binding to cultured endothelium was quantified by prelabeling the cells with $^{125}$I; the inhibitory effects of anti-$\beta$ are illustrated in FIG. 11.

Different cell adhesion molecules are expressed in different tissues in response to a variety of stimuli. Brain-specificity may be beneficial in administering a leukocyte adhesion modulator for therapeutic purposes. The VLA-4 leukocyte adhesion molecule is known to be expressed throughout the body under various conditions. Other tissues, apart from brain tissue, were analyzed in order to determine if either the anti-$\alpha$-4 or the anti-$\beta$-1 antibody had any immune reaction in those tissues. As shown in more detail in Example 22, the anti-$\alpha$-4 inhibited lymphocyte binding to normal intestinal lymphoid tissue, but did not affect binding to normal lymph nodes. The anti-$\beta$-1 antibody does not inhibit binding to lymph nodes and would not be expected to affect binding to intestinal lymphoid tissue.

VLA-4 is a member of the $\beta 1$ integrin family of cell adhesion molecules, each of which is comprised of two subunits, an $\alpha$ and a $\beta$ chain. There are at least six $\beta 1$ integrins, all sharing the same $\beta 1$ chain and each having a distinct $\alpha$ chain. These six receptors all bind a different complement of the various cell matrix molecules, such as fibronectin, laminin, and collagen. VLA-4, for example, binds to fibronectin. VLA-4, however, is unique in that it also binds to a non-matrix molecule that is expressed by endothelial cells. This molecule is called VCAM-1, and is thought to be expressed on endothelium at various geographic locations in response to various stimuli. Distinct epitopes of VLA-4 are responsible for the fibronectin and VCAM-1 binding activities, and each activity can be inhibited independently.

One of the monoclonal antibodies presently used, HP2/1 reacts with the $\alpha$ chain of VLA-4 and blocks only its binding to VCAM-1. It does not affect binding of VLA-4 to fibronectin, nor does it affect the activity of the other members of the $\beta 1$ integrin family. However, the $\alpha$ chain of VLA-4 also interacts with a distinct $\beta$ chain, called $\beta$p. This receptor mediates all lymphocyte binding to intestinal lymphoid tissues. Another of the antibodies used, the monoclonal antibody, HP2/1, reacting with VLA-4$\alpha$ blocks the activity of this molecule, i.e., it prevents the binding of VLA4$\alpha\beta$p to intestinal endothelium (illustrated in Table 12). The monoclonal antibody, AIIB2 reacts with the $\beta 1$ chain that is common to all members of the $\beta 1$ integrins and potentially immunoreacts with the entire family, including the fibronectin and the VCAM-1 binding activities of VLA-4. It would not be expected to inhibit lymphocyte binding to intestinal endothelium, however, because it would not bind to $\beta$p.

Reagents which selectively react against the VLA-4/VCAM-1 target are also envisioned. For example, an antibody which interacts with the VCAM-1 binding domain of VLA4$\alpha$ in conjunction with the $\beta 1$ chain would block only lymphocyte migration into sites of inflammation, such as the brain during multiple sclerosis. This reagent further would not affect matrix interactions (mediated by all members of the $\beta 1$ integrins) nor would it affect normal intestinal immunity (mediated by VLA-4$\alpha\beta$p). The production of this, and other such reagents is well within the skill of the art.

B. VLA-4/VCAM-1 Directed Cell Adhesion Modulators And Uses

The VLA-4/VCAM-1 molecules, instrumental in brain inflammation (particularly MS-type brain inflammation) provide molecular targets that can be put to a variety of uses. The present invention thus encompasses these uses and related compositions.

First, as is shown by Example 23, receptors against the VLA-4 ligand may be used to modulate leukocyte adhesion to brain endothelial cells. Herein, the term "receptor" is used to denote a biologically active molecule that binds to a ligand. For example, antibodies or fragments thereof, which immunoreact with the VLA-4 molecule may be useful to prevent leukocyte binding to brain endothelial cells. Peptides, or peptidomimetics or related compounds, which can act to bind the cellular adhesion molecule, are also contemplated, and these may be made synthetically by methods known in the art. Other receptors which react with a VLA-4 ligand will be apparent to those skilled in the art.

Additionally, receptors against a VCAM-1 ligand may be used to modulate leukocyte adhesion to brain endothelial cells. Either way, one cell adhesion molecule is blocked, and one pathway of leukocyte adhesion is terminated.

It should be recognized that for therapeutic purposes, therapeutically effective compositions for preventing or ameliorating brain inflammation containing such VLA-4 or VCAM-1 directed receptors are contemplated as within the scope of the present invention. For example, therapeutic compositions including at least one VLA-4 receptor or VCAM-1 receptor as well as other therapeutic compositions could be used to prevent or ameliorate inflammation of brain endothelial cells. Another example is the use of a VCAM-1 receptor, to which is attached a drug useful for treating MS or other inflammatory condition, for a drug delivery vehicle which also prevents the adhesion of leukocytes to the VCAM-1 molecule. Peptides or peptidomimetics or other molecules, which serve to substantially mimic one cell adhesion molecule or the other, could be used in competition therapy wherein such peptides or peptidomimetics (or other compounds) compete for the available locations on the surface of either the leukocyte (if substantially mimicking VCAM-1) or the endothelial cell (if substantially mimicking VLA-4).

Suitable pharmaceutical carriers and their formulations are described in Martin, Remington's Pharmaceutical Sciences, 15th Ed. (Mack Publishing Co., Easton 1975). Such compositions will, in general, contain an effective amount of the active compound together with a suitable amount of carrier so as to prepare the proper dosage form for proper administration to the host. Useful pharmaceutical carriers for the preparation of the pharmaceutical compositions hereof can be solids, liquids or gases; thus, the compositions can take the form of tablets, pills, capsules, powders, enterically coated or other protected formulations (such as by binding on ion exchange resins or other carriers, or packaging in lipid protein vesicles or adding additional terminal amino acids), sustained release formulations, solutions (e.g., ophthalmic drops), suspensions, elixirs, aerosols, and the like. Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like.

In the practice of the therapeutic methods of the present invention, an effective amount of the active compound, including derivatives or salts thereof, or a pharmaceutical composition containing the same, as described above, is administered via any of the usual and acceptable methods known in the art, either singly or in combination with another compound or compounds of the present invention or other pharmaceutical agents such as anti-inflammatory agents, or other therapeutics known to have an effect on inflammation or the like. These compounds or compositions can thus be administered orally, sublingually, topically (e.g., on the skin or in the eyes), parenterally (e.g., intramuscularly, intravenously, subcutaneously or intradermally), or by inhalation, and in the form of either solid, liquid or gaseous dosage including tablets, suspensions, and aerosols, as is discussed in more detail above. The administration can be conducted in single unit dosage form with continuous therapy or in single dose therapy ad libitum.

In one preferred embodiment, the therapeutic methods of the present invention are practiced when the relief of symptoms is specifically required or perhaps imminent; in another preferred embodiment, the method hereof is effectively practiced as continuous or prophylactic treatment.

In the practice of the therapeutic methods of the invention, the particular dosage of pharmaceutical composition to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. It is presently believed that dosages in the range of 0.1 to 100 mg of compound per kilogram of subject body weight will be useful, and a range of 1 to 100 mg per kg generally preferred, where administration is by injection or ingestion. Topical dosages may utilize formulations containing generally as low as 0.1 mg of compound per ml of liquid carrier or excipient, with multiple daily applications being appropriate.

Imaging reagents are also contemplated. A tracer molecule, detectable in radiographic or other imaging techniques) could be linked to an anti-VCAM or anti-VLA-4 reagent to identify areas of active leukocyte traffic in the brain. This is useful in diagnostic protocols and in determining the progression of the disease or the effectiveness of therapy, for example.

Other uses, formulations, compositions, and processes will be readily apparent to those skilled in the art.

The following examples are illustrative of several embodiments of this invention, and should not be construed as in any way limiting the invention as recited in the claims.

EXAMPLE 1

Electrical Resistance of Endothelial Cell Cultures Treated with Cyclic AMP

Bovine brain capillary endothelial cells were grown on polycarbonate filters in a conditioned growth medium containing either 5% or 10% PDHS. In controls, the growth medium contained 5% PDHS (□) or 10% PDHS (■). In experimental cultures, the growth medium was supplemented with either 5% PDHS+250 $\mu$M 8-(4-chlorophenylthio) cyclic AMP (○) or 10% PDHS+250 $\mu$M 8-(4-clorophenylthio)cyclic AMP+35 $\mu$M RO-20-1724, a cyclic AMP phosphodiesterase inhibitor (●). Transmonolayer electrical resistances were then determined; these are shown in FIG. 1.

The cyclic AMP analogue alone greatly increased transmonolayer electrical resistance, which is indicative of tight junction formation. Resistances of about 400 ohm-cm$^2$, were obtained with monolayers treated with both the cyclic AMP analogue and an agent (RO-20-1724) that inhibited degradation of cyclic AMP.

EXAMPLE 2

Figure 2:
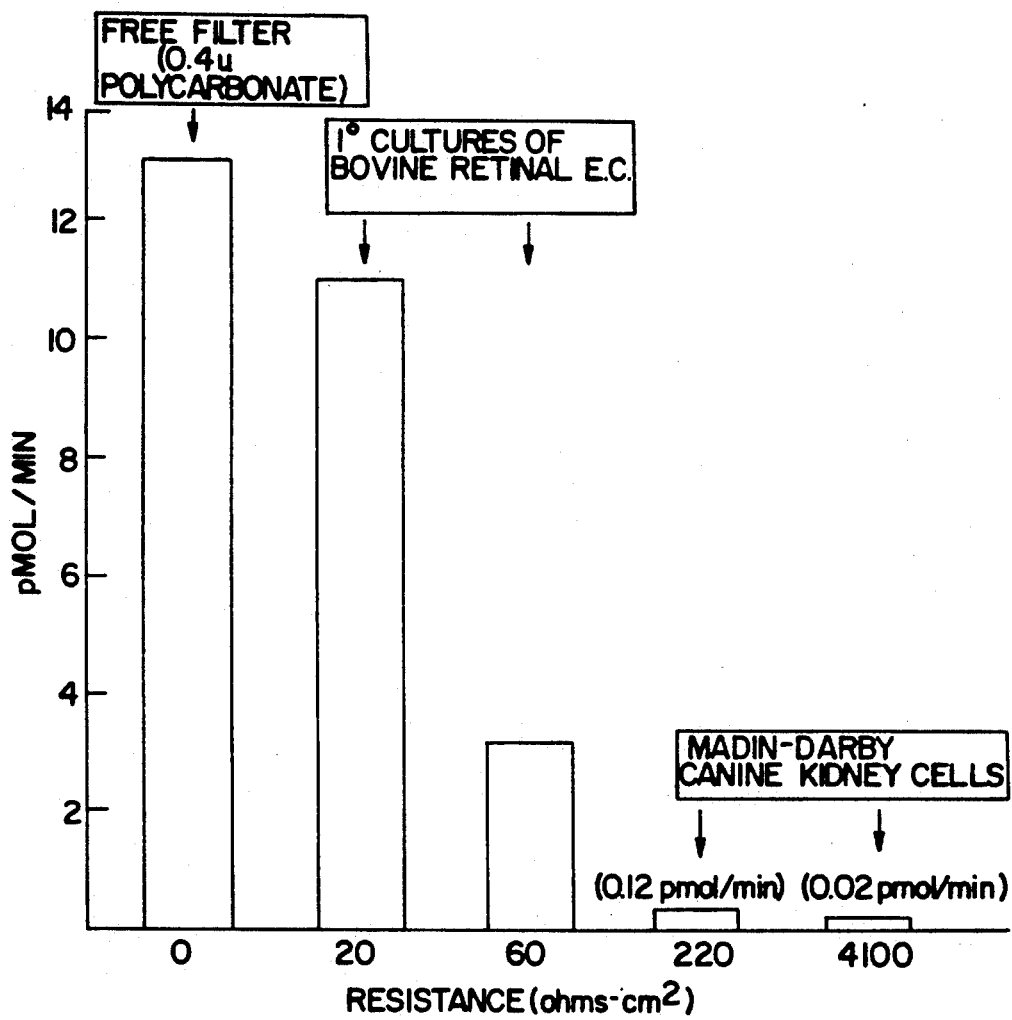
FIG. 2 provides albumin flux data for monolayer cultures of bovine retinal endothelial cells and MDCK epithelial cells.

Transport of Labeled Albumin Across Endothelial Cells as a Function of Transmonolayer Electrical Resistance The flux of $^{125}$I-labeled albumin across monolayers of primary cultures of bovine retina endothelial cells and of Madin-Darby Canine Kidney epithelial cells disposed on 0.4$\mu$ pore-sized polycarbonate filters was determined as a function of tight junctions as reflected in trans-monolayer electrical resistance of each cell type. The results of such experiments are plotted in FIG. 2. The height of the bars in the histogram is a reflection of leakage of albumin through the junctions between cells—the higher the bar, the greater the leakage of albumin.

Control cell-free filter, of course, exhibited the smallest impediment to albumin flux.

Substantial flux of albumin across monolayers of bovine retina cells occurred when the electrical resistance was only 20 ohm-cm², and this flux was reduced by 75% in cultures exhibiting an electrical resistance of 60 ohm-cm².

In contrast, the flux of albumin was virtually abolished in monolayers of MDCK cells in which transmonolayer electrical resistances of greater than 200 ohm-cm² were observed.

EXAMPLE 3

Effects of Various Agents on Transendothelial Cell Electrical Resistance

Bovine brain capillary endothelial cells were grown to substantial confluency on either 3 μm polycarbonate or 0.4 μm nitrocellulose filters.

Cultures were either untreated for 24 hours (control) or grown for 24 hours in a growth medium containing either 250 μM 8-(4-chlorophenylthio) cyclic AMP+35 μM RO-20-1724 (cAMP) or these two agents plus 50% (w/v) bovine aortic endothelial cell-derived conditioned medium (cAMP - BAEC-CM). Transmonolayer electrical resistances were then determined. The results are shown in Table 1.

TABLE 1

| Treatment | Filter | Resistance (ohm-cm²) |
|---|---|---|
| Control | 3 μm polycarbonate | 38 |
| cAMP | 3 μm polycarbonate | 205 |
| cAMP + BAEC-CM | 3 μm polycarbonate | 348 |
| Control | 0.4 μm nitrocellulose | 94 |
| cAMP + BAEC-CM | 0.4 μm nitrocellulose | 320 |

The results indicate that cAMP alone produced about a 6-fold increase in transmonolayer resistance, to about 00 ohm-cm². The combination of BAEC-CM and cAMP increased resistance by about 10-fold, to about 350 ohm-cm², on polycarbonate filters.

EXAMPLE 4

Effects of Elevation of Intracellular Cyclic AMP Concentration on Transendothelial Cell Electrical Resistance Bovine brain capillary endothelial cells were grown essentially to confluency on 0.4 μm polycarbonate filters.

Cultures were either untreated for 24 hours (Control) or treated for 24 hours with 250 μM 8-(4-chlorophenylthio) cyclic AMP (cAMP), 10 μM isoproterenol (ISO), 10 μM 5-hydroxytryptamine (5-HT), or 10 μM forskolin. In all cultures, 35 μM RO-20-1724 was also present. Transmonolayer electrical resistances were then determined. Each value in Table 2 represents the average of 3 replicate experiments, referred to control cells to which was assigned a resistance value of 100.

TABLE 2

| Treatment | Relative Resistance |
|---|---|
| Control | 100 |
| cAMP | 465 |
| ISO | 439 |
| 5-HT | 586 |
| Forskolin | 834 |

The results indicated that any agent that elevated effective intracellular cyclic AMP concentrations enhanced transmonolayer electrical resistance by at least 4-fold. The greatest enhancement of resistance (over 8-fold) was obtained by the use of forskolin, a compound that activates adenylate cyclase directly.

EXAMPLE 5

Effects of Cyclic AMP, Conditioned Medium and Astrocyte Extracellular Matrix on Transendothelial Cell Electrical Resistance Bovine brain capillary endothelial cells were grown to essential confluency on nitrocellulose or polycarbonate filters. In A and B, the filters were first coated with type I collagen and fibronectin. In C and D, type I astrocytes from neonatal rat brain were then grown to confluency on these collagen and fibronectin-coated filters. In case C, the astrocytes were lysed in 1% Triton X-100 in 5 mM Tris buffer, pH 7.5, for 30 min. at 25 C. The filters were rinsed again in PBS. In case D, astrocytes were grown as in case C, but then treated with 5 mM EDTA in PBS for 30 min. at 37° C. to remove the cells. These filters were also treated with 25 mM NH₄OH and rinsed in PBS. Bovine brain endothelial cells were grown to confluency on these different types of filters. In B, C and D, cells were treated as in Table 1 with 250 μM 8-(4-chlorophenylthio) cyclic AMP (cAMP), 35 μM 35 μM RO-20-1724 and bovine endothelial cell conditioned medium (BAEC-CM). Transendothelial electrical resistances were determined; resistances were normalized to a control value of 100 in Table 3.

The combination of the cyclic AMP derivative, phosphodiesterase inhibitor and BAEC-CM produced a substantial increase in transmonolayer electrical resistance. These effects were further potentiated when the cells were grown on astrocyte extracellular matrix prepared as described in C. When cells were grown on astrocyte extracellular matrix prepared as in D, they did not grow to confluency (and, hence, the transmonolayer resistance was low). When cells were grown on matrices prepared from other cell types (such as endothelial cells), there was no increase in resistance.

TABLE 3

| Treatment | Relative Resistance |
|---|---|
| A) Control | 100 |
| B) cAMP + BAEC-CM | 980 |
| C) cAMP + BAEC-CM + astro-ECM #1 | 2652 |
| D) cAMP + BAEC-CM + astro-ECM #2 | 138 |

EXAMPLE 6

Effect of Astrocyte-Derived Conditioned Medium on Electrical Resistance of Brain Endothelial Cells Freshly-dissociated bovine brain endothelial cells (BBEC) were plated on tissue culture dishes either in the absence or presence of astrocyte-derived conditioned medium (ADCM). Cells were then plated onto collagen-fibronectin-coated filters, again in the absence or presence of ADCM. After the cells reached confluency, samples were treated with 250 μM 8-(4-chlorophenylthio) cyclic AMP and 35 μM RO-20-1724 (+cAMP in Table 4).

The data of Table 4 demonstrate that the highest resistances were obtained when cells were placed initially in ADCM.

TABLE 4

| Growth Medium* | Plating Medium | Electrical resistance | |
|---|---|---|---|
| | | − cAMP | + cAMP |
| | | ohm-cm² | |
| MEM/FCS | MEM/FCS | 11 | 42 |
| 50% MEM/FCS: 50% ADCM | MEM/FCS | 12 | 142 |
| MEM/FCS | 50% MEM/FCS: 50% ADCM | 27 | 160 |
| 50% MEM/FCS: 50% ADCM | 50% MEM/FCS: 50% ADCM | 46 | 312 |

*MEM, minimal essential medium; FCS, fetal calf serum; ADCM, astrocyte-derived conditioned medium.

EXAMPLE 7

Effect of Fetal Calf Serum Reduction on Electrical Resistance of Brain Endothelial Cells Bovine brain endothelial cells were dissociated and plated on tissue culture dishes in 50% MEM/FCS - 50% ADCM. Cells were then passaged onto collagen-fibronectin-coated filters and grown in the media indicated in Table 5. Conditions were as in Example 6, except that some cells were grown in 50% serum-free defined medium (N2). The results are shown in Table 5.

The data demonstrate that the highest resistance were attained with cells grown in ADCM and cyclic AMP analogues in the presence of reduced fetal calf serum. The same result was obtained when the defined medium N2 was replaced by MEM.

TABLE 5

| Treatment of cells* | Resistance ohm-cm² |
|---|---|
| MEM/FCS | 40 ± 6 |
| + cAMP | 163 ± 22 |
| + ADCM | 56 ± 15 |
| + cAMP + ADCM | 345 ± 64 |
| 50% MEM/FCS, 50% N2 | 61 ± 2 |
| + cAMP | 305 ± 50 |
| + ADCM | 115 ± 11 |
| + cAMP + ADCM | 625 ± 82 |

*MEM, minimal essential medium; cAMP, cyclic AMP; ADCM, astrocyte-derived conditioned medium.

EXAMPLE 8

Transport Data Across High Resistance Monolayers

Figure 3:
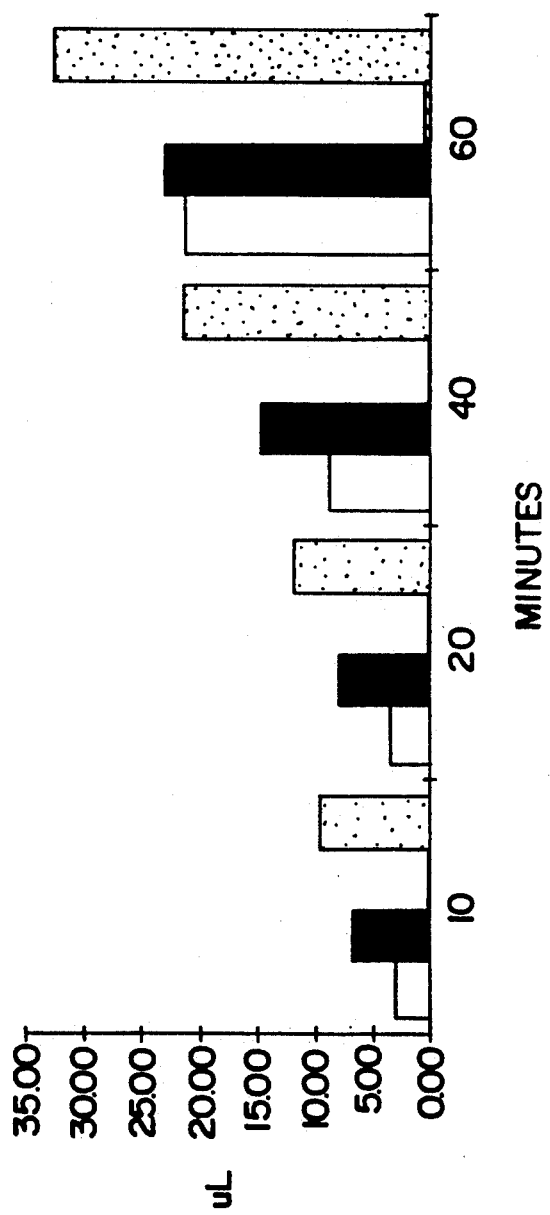
FIG. 3 shows flux data for sucrose and chlorambucil across tight junction brain endothelial cells.

FIG. 3 shows transport data across high resistance monolayers of bovine endothelial cells on filters in the blood-brain model of the invention, using labeled sucrose (360 dalton, hydrophilic) and labeled chlorambucil (304 dalton, mildly hydrophobic anti-tumor compound).

Although these compounds are of similar size, the hydrophobic compound was transported much better than was the hydrophilic compound across filters with cells, compared to transport rate across cell-free filters.

Sucrose was almost entirely prevented from leaking between the cells. This is a significant advance over previous models in which the difference in the rate of sucrose across filters with and without cells was 3 to 5-fold due to leaky tight junctions in those models.

EXAMPLE 9

Effects of Protein Kinase Inhibitors on Resistance of Brain Endothelial Cells

Bovine brain endothelial cells were grown to confluency on filters in the blood-brain model of the invention as described in Examples 1, 3 and 5 above, and the effects of protein kinase inhibitors K252a and staurosphorine on resistance determined. These compounds are non-specific in that they inhibit protein kinases A and C, MLCK, etc. The results are shown in Table 6.

TABLE 6

| Drug | Resistance (% of control) | | |
|---|---|---|---|
| | 1 hr. | 2.5 hr. | 24 hr. |
| K252a (200 nM) | 79 | 25 | 24 |
| Staurosporine | | | |
| 10 nM | 108 | 20 | 5.2 |
| 30 nM | 64 | 7.7 | 2.3 |
| 100 nM | 5.5 | 0 | 0 |

Both compounds, but particularly staurosporine, were remarkably effective in reducing resistance, i.e., opening up tight junctions. The effects of both inhibitors were reversible.

At the light microscope level, either removing cyclic AMP or adding a protein kinase inhibitor caused clear separation of endothelial cell tight junctions.

EXAMPLE 10

Effect of Brain Kinase Inhibition on Brain Uptake In Vivo

Staurosporine was administered by intracarotid infusion. The transport of $^3$H-sucrose and $^{125}$I-BSA was then determined. The data in Table 7 represent the amount of radioactivity remaining in the brain after infusion and washout. An average of 3-4 animals was used in each category.

TABLE 7

| | $^3$H-Sucrose | $^{125}$I-BSA |
|---|---|---|
| | Experiment 1 (DPM) | |
| Saline control | 6.2 × 10³ | 178 |
| Staurosporine | 24.3 × 10³ | 835 |
| | Experiment 2 (DPM) | |
| Saline control | 1.4 × 10³ | 98 |
| Staurosphorine | 8.7 × 10³ | 520 |

The results showed that staurosporine enhanced entry into the brain of both small (sucrose) and large (BSA) molecules, as the result of the inhibitance of the activity of cyclic AMP-activated protein kinase.

EXAMPLE 11

Effect of Gi Receptor Agonists and Agents That Increase Cyclic GMP on Blood-Brain Barrier in an In Vivo Test System The test compound was delivered to a restrained, unanesthetized mouse (30-35 g) via the tail vein. The injectate also contained 10 μCi $^3$H-sucrose and 1 μCi $^{125}$-BSA as tracer substances that do not normally penetrate the BBB in vivo. Fifteen or sixty minutes after the injection, the animal, anesthetized with 2% Avertin, was perfused via venipuncture with phosphate buffered saline followed by fixative. The brain was removed immediately, the medulla, pons and hypothalamus excised and the remaining tissue homogenized by passsage through a 3 cc needle into a preweighed scintillation vial containing 1.5 ml Soluene (Packard). The vial was weighed to determine wet tissue weight. Ten ml of Inst-Gel (Packard) was added to each sample after overnight incubation at 75° C. The samples were counted for DPM by liquid scintillation spectrometry.

Values are expressed as DPM/gm tissue. A minimum of four animals/group were used for each experiment. Data are expressed as the mean fold-increase which is derived by dividing the treatment value by the control value. Numbers in parenthesis represent the number of experiments carried out for the particular condition.

TABLE 8

| Compound | | Radioactivity (DPM) | |
|---|---|---|---|
| | | $^3$H-sucrose | $^{125}$I-BSA |
| CPA, 100 ug/kg | 15' | 1.6 (2) | 1.2 (2) |
| | 60' | 2.6 (2) | 1.9 (2) |
| R-PIA, 25 ug/kg | 15' | 2.0 (1) | 1.2 (1) |
| | 60' | 3.0 (2) | 1.8 (2) |
| Nitroprusside, 3 mg/kg | 15' | 1.5 (1) | 1.0 (1) |
| | 60' | 2.3 (2) | 1.2 (2) |

The results show that adenosine Gi receptor agonists (such as cyclopentyladenosine, CPA) and the (−) stereoisomers of $N_6$-(phenylisopropyl)-adenosine (R-PIA) increased the uptake by brain of small (sucrose) and large (BSA) molecules by as much at 300%.

EXAMPLE 12

Effect of Tight Junction Permeability Modulators on Behavioral Assay

The behavorial assay is designed to demonstrate delivery of a drug into the brain parenchyma at levels sufficient to have a therapeutic effect. Morphine and the naturally occurring opioid peptides, endorphin and enkephalin, bind to $\mu$ opioid receptors in the brain and suppress the sensation of pain. This analgesic effect can be demonstrated with mice in the hot plate assay. Mice are placed on a surface uniformly heated to 55° C. The time it takes for the mouse to respond to the heat stimulus by licking its front or hind paws is measured. Morphine (700 MW) delivered by i.v. injection at doses of 1–10 mg/kg, has an analgesic effect in that it increases the latency of response to the heat stimulus measured 15 minutes after the injection. The latency is expressed as % analgesia.

$$\% \text{ analgesia} = \frac{(t_e - t_c) \times 100}{(T - t_c)}$$

Figure 4:
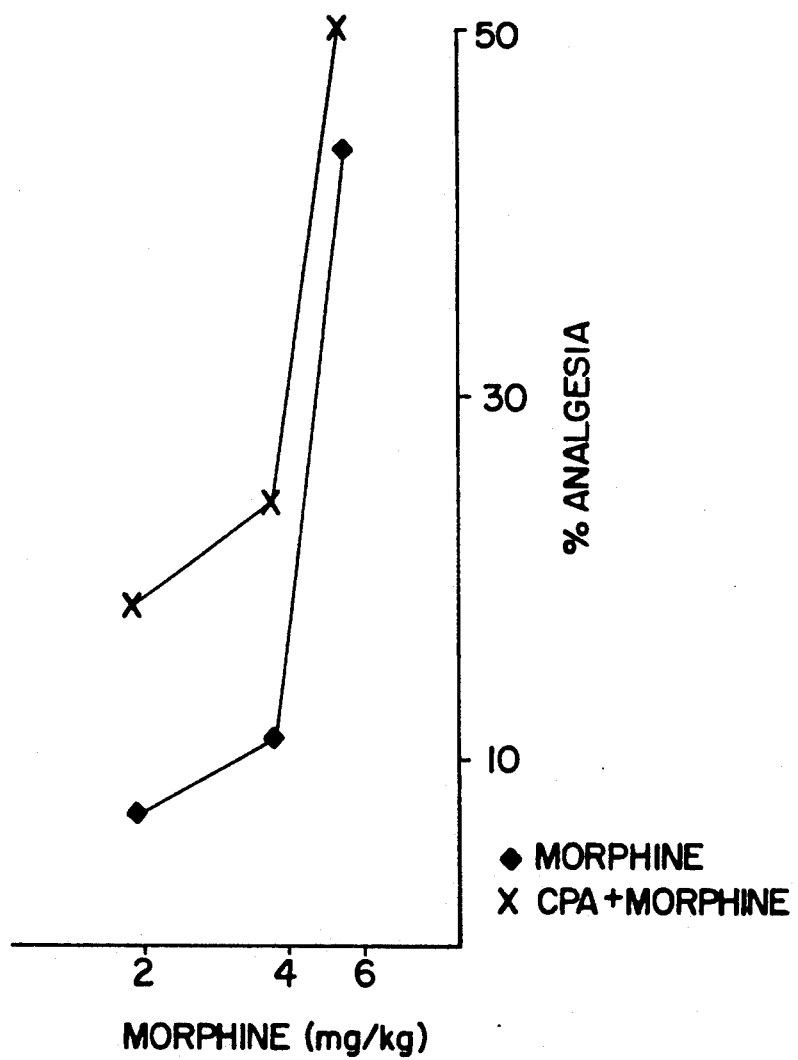
FIG. 4 shows the effect of agents that lower cyclic AMP concentrations on morphine analgesia in animals.

$t_e$ = experimental latency at given dose of analgesic
$t_c$ = control latency with no analgesic
$T$ = 60 sec., the maximum allowed latency The purpose of these experiments is to test the ability of putative BBB openers to shift the morphine dose response curve to lower doses and thus have analgesic activity when delivered peripherally. In this experiment (FIG. 4) 25 μg/kg of CPA potentiated the effects of morphine, particularly at lower morphine levels. ●, morphine alone; x, CPA+morphine Thus, CPA, which reduces cyclic AMP production, lowered the amount of morphine that had to be administered to produce analgesia, i.e., CPA opened the blood-brain barrier.

EXAMPLE 13

Inhibition by Nitroprusside of Effect of Cyclic AMP on Endothelial Cell Tight Junctions Confluent layers on filters of bovine brain endothelial cells not previously treated with cyclic AMP analogues were stimulated with RO-20-1724 (+RO in FIG. 5) at the beginning of the experiment so as to increase cyclic AMP levels and resistance or left untreated (−RO). Other cultures were treated with RO-20-1724 plus sodium nitroprusside (NitroP) in various concentrations. Nitroprusside is known to increase the activity of the Gi system. The resistance of the cells was then determined as above.

Figure 5:
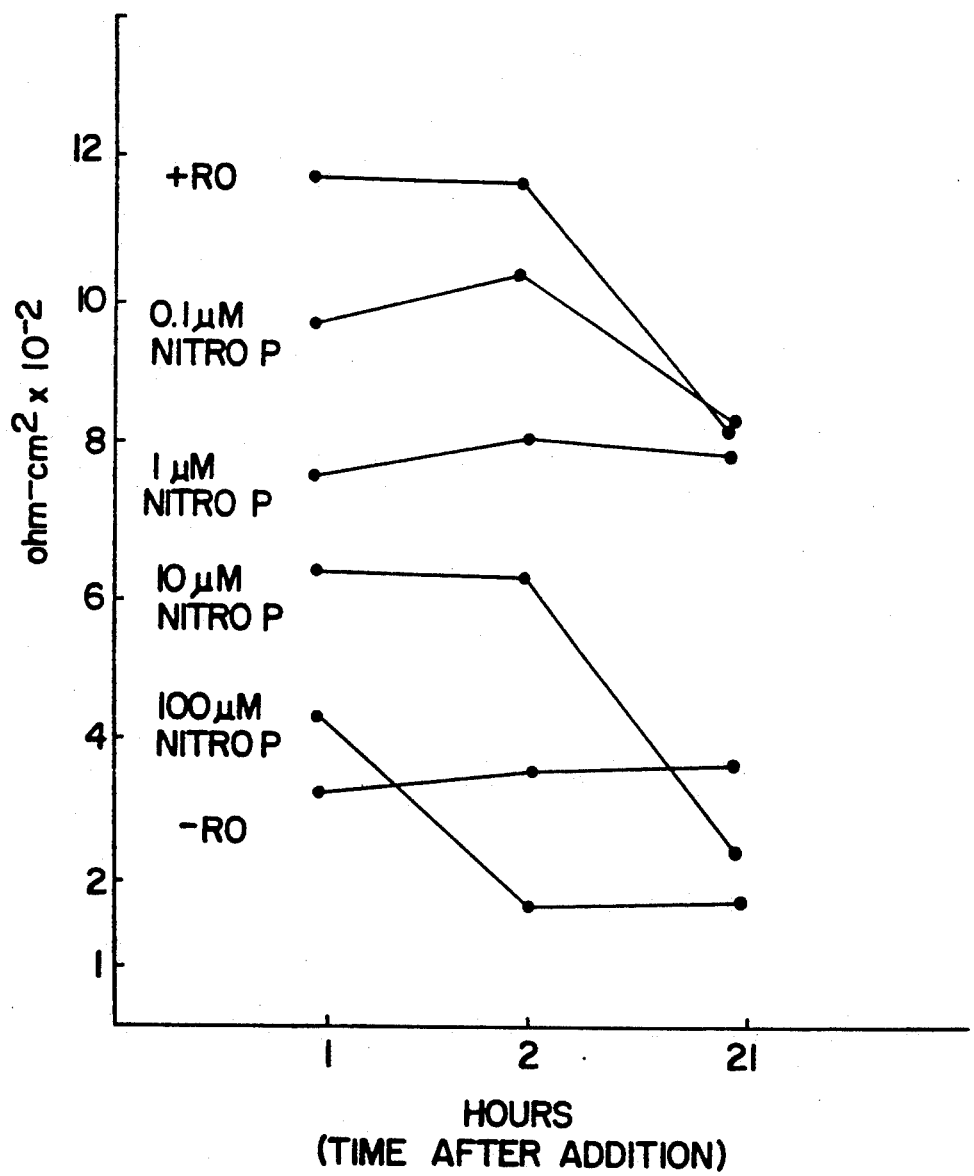
FIG. 5 shows the effects of elevating endothelial cell levels of cyclic GMP on cyclic AMP-induced tight junctions.

The results, shown in FIG. 5, show that nitroprusside inhibited the increase in resistance produced by cyclic AMP elevation in a dose-dependent manner.

EXAMPLE 14

Effect of Sodium Nitroprusside on Morphine-Induced Analgesia

Figure 6:
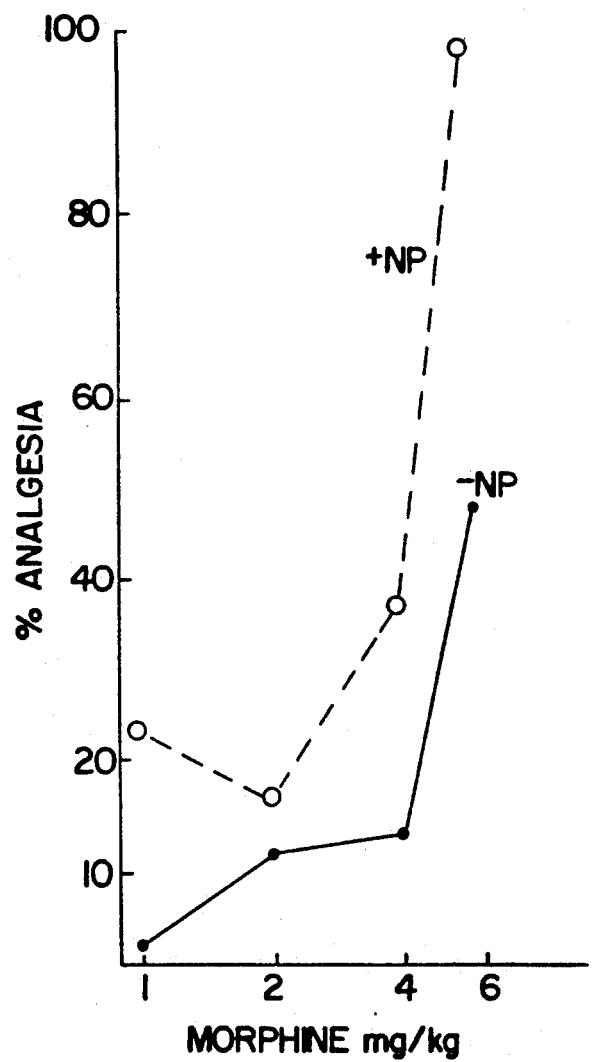
FIG. 6 shows the effects of elevating in vivo levels of cyclic GMP on morphine analgesia.

The effects of sodium nitroprusside, an agent that increases cyclic GMP levels, on morphine-induced analgesia in mice were determined by the assay system of Example 12, and are shown in FIG. 6. Nitroprusside (+NP) decreased the amount of morphine required to produce analgesia, suggesting that the former opened up the blood-brain barrier to the latter.

EXAMPLE 15

Appearance of E-Cadherin on Endothelial Cells

Bovine brain endothelial cells were grown to confluency on filters either in control medium (low resistance cultures) or under conditions of enhanced cyclic AMP plus endothelial cell conditioned medium as in Examples 1, 3 and 5 (high resistance cultures). After transendothelial cell resistance measurements, cultures were fixed and labeled with a rabbit antibody prepared against mouse E-cadherin with a fluorescent FITC-conjugate of goat anti-rabbit immunoglobulin. The high resistance cultures stained much more brightly for E-cadherin than did low resistance cultures, and also showed some localization of the E-cadherin around cell borders. As E-cadherin appears to be expressed specifically in endothelial cells in brain, these observations are a further demonstration that treatments that increase electrical resistance of brain endothelial cells in culture also cause them to adopt another characteristic property of the BBB.

EXAMPLE 16

Effect of Inhibition of Cyclic GMP Phosphodiesterase on Enkephalin-Induced Analgesia The behavioral assay described in Example 12, modified to induce analgesia with an endogenous opiate, enkephalin (20 mg/kg), rather than with morphine, was applied to mice treated with the cyclic GMP phosphodiesterase inhibitor, dipyridamole. The results are shown in Table 9.

TABLE 9

| | Percent Analgesia | |
|---|---|---|
| Experiment | Enkephalin | Enkephalin + Dipyridamole |
| 1 | 2.8 | 13.5 |
| 2 | 6.4 | 25.8 |

These results are consistent with the theory that elevation of intracellular levels of cyclic GMP increase the permeability of brain microvascular endothelial cell tight junctions to morphine.

EXAMPLE 17

Effect of Inhibition of Cyclic GMP Phosphodiesterase on Blood-Brain Barrier in an In Vivo Test System The in vivo tracer experiment of Example 11 was repeated, except that the test compound was the cyclic GMP phosphodiesterase inhibitor, dipyridamole.

TABLE 10

| Condition | Time min. | DPM/gm tissue | |
|---|---|---|---|
| | | $^3$H-sucrose | $^{125}$I-BSA |
| Control | 15 | 8,757 ± 2034 | 616 ± 46 |
| Dipyridamole | 15 | 18,233 ± 4770 | 1110 ± 187 |
| Control | 60 | 12,164 ± 1774 | 579 ± 47 |
| Dipyridamole | 60 | 17,932 ± 2642 | 943 ± 157 |

The results show that inhibition of cyclic GMP phosphodiesterase, which results in an elevation of intracellular levels of cyclic GMP, increased the transport across the blood-brain barrier of both small (sucrose) and large (bovine serum albumin) molecules.

EXAMPLE 18

Effects of Different Classes of Phosphodiesterase Inhibitors on Brain Microvascular Endothelial Cell Tight Junctions In Vitro Bovine brain microvascular endothelial cells were isolated and grown on permeable filters in the BBB in vitro model of the invention. Cells were maintained in astrocyte-derived conditioned medium, but were not treated with agents that elevate cyclic AMP levels in such cells.

Figure 7A:
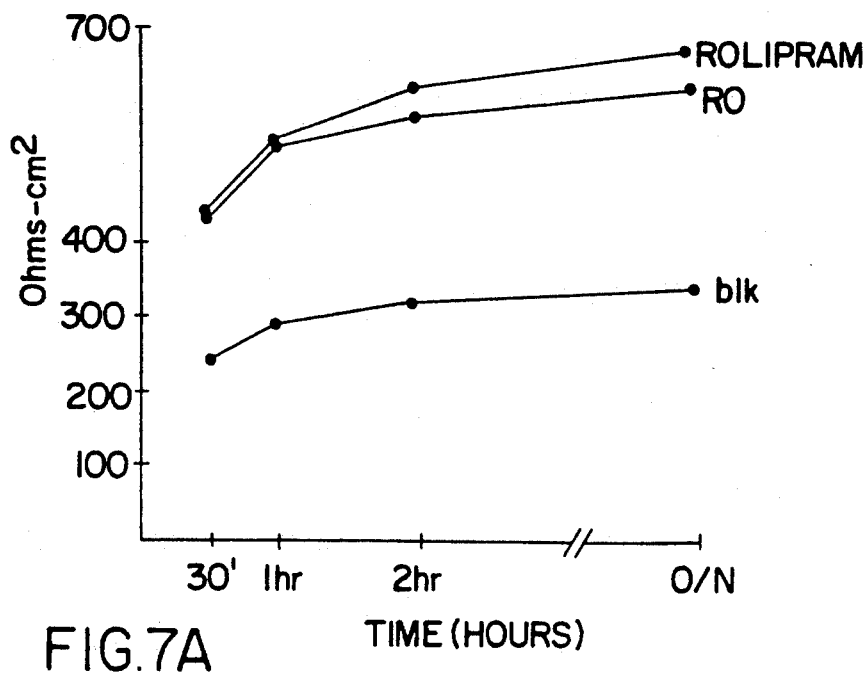
FIG. 7 shows the effects of different classes of cyclic AMP phosphodiesterase inhibitors on tight junctions of brain endothelial cells in the BBB in vitro model.
Figure 7B:
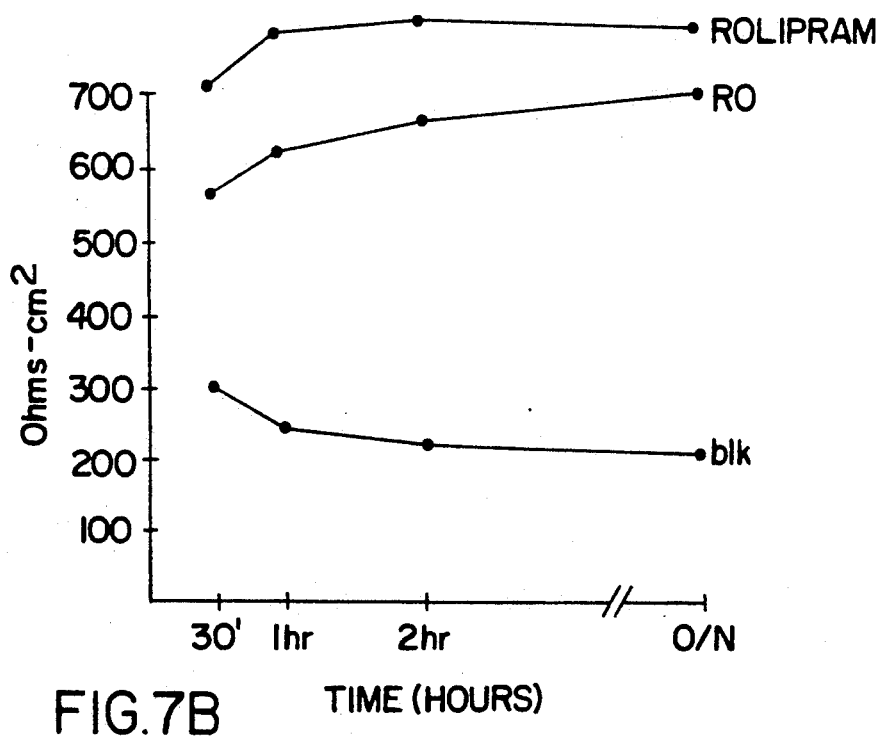

At the beginning of the experiment (i.e., in a low resistance state), cells were either left untreated (blk in FIG. 7) or treated with 17.5 μM Rolipram or RO-20-1724 (RO in FIG. 7) (specific inhibitors of cyclic AMP phosphodiesterase). Resistance was then measured at various times. In both experiments (FIG. 7), by 30 minutes resistance was already substantially higher in cells treated with these compounds. In contrast, specific inhibitors of cyclic GMP phosphodiesterase, zaprinast, dipyridamole and milrinone, were ineffective under analogous conditions. This suggests that the phosphodiesterase predominantly responsible for degrading cyclic AMP in brain endothelial cells is a Type III cyclic GMP-noninhibitable phosphodiesterase. This also suggests that inhibitors of this class of enzyme may be effective in treating vasogenic brain edema.

EXAMPLE 19

Resistance of Human Brain Microvascular Endothelial Cells in an In Vitro Blood-Brain Barrier Model Brain biopsy specimens from human epileptic patients were transported from the operating room to the laboratory in a MEM-antibiotic medium. After dissecting away the meninges, gray matter was rinsed, then homogenized in L-15 medium as described above. The homogenate was passed through a 50 μm nylon filter; the residue was passed through a 50 μm filter twice more. The final residue was spun down, then suspended in 5 ml of a solution containing collagenase, trypsin and DNAse, as described above for bovine brain endothelial cells. Isolated capillary fragments and cells were centrifuged, resuspended and plated on collagen-fibronectin-coated flasks in a growth medium containing rat astrocyte-derived conditioned medium. The cells were then maintained as described above for bovine brain cells.

After the cells had been transferred to permeable supports and grown to confluency, some were treated with chlorophenyl-thio-cyclic AMP+RO-20-1724 as detailed above.

Prior to elevation of cyclic AMP levels, resistance of the cells (average of six replicates) was 62.5 ohm-cm$^2$. Subsequent to treatment, resistance of the cells (average of six replicates) averaged 357.8 ohm-cm$^2$.

This experiment demonstrated that human brain microvascular endothelial cells responded as did the counterpart cells from bovine brain in terms of tight junction formation in response to cyclic AMP.

EXAMPLE 20

Effect of Removal of Cyclic AMP-Elevated Agents on the Subsequent Resistance of Brain Microvascular Endothelial Cells Bovine brain endothelial cells were grown to confluency on filters in the blood-brain barrier of the invention using the standard protocol described in Examples 1, 3 and 5. Thereafter, cells were treated for 48 hours with chlorophenyl-thio-cyclic AMP+RO-20-1724. The medium containing these cyclic AMP elevating agents was removed, and the cells were washed with fresh growth medium. To some cells was added growth medium alone, and to other cells was added growth medium containing the cyclic AMP analogue and RO-20-1724. The resistance of the cell monolayers was measured periodically, and the results are shown in Table 11.

TABLE 11

| Time of second incubation min. | Resistance | |
|---|---|---|
| | Medium alone | Medium + "cyclic AMP" |
| | ohm-cm$^2$ (average) | |
| Initial | 322 | 322 |
| 15 | 74 | 212 |
| 30 | 69 | 284 |
| 60 | 59 | 293 |
| Overnight | 39 | 332 |

Resistance dropped quite rapidly when intracellular levels of cyclic AMP were reduced (Medium alone in Table 11), due, probably, to the presence of a rapidly acting phosphoprotein phosphatase that dephosphorylates cyclic AMP-activated proteins. Resistance remained high when washed cells continued to be exposed to sources of intracellular cyclic AMP (Medium+"cyclic AMP").

EXAMPLE 21

Modulation of Leukocyte Adhesion to Inflamed Brain Endothelial Cells

In this preferred embodiment, antibodies against VLA-4 were shown to substantially prevent leukocyte adhesion to brain endothelial, using both a novel system for inducing MS-type inflammation in vivo, and the blood brain barrier model.

Unless otherwise stated, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. As set forth above, all publications to which reference is made are incorporated herein by reference.

Materials and Methods

Lymphocytes: Mouse or rat lymphocytes were isolated immediately before a binding assay from mesenteric, cervical and brachial lymph nodes by standard methods and crushed between the frosted ends of two glass slides. Human lymphocytes were isolated from heparinized or EDTA-treated whole blood using Mono/Poly separation medium (Flow Labs, Mclean, Va.), and used immediately.

Lymphoid Cell Lines: All cell lines were obtained from the cell culture facility at the University of California, San Francisco and were maintained in RPMI-1640 with 10% FBS (37° C., 10% CO2). RPMI-1460 was purchased from the University of California, San Francisco. These University of California cell lines are all made available to the public. Specifically, the cell lines obtained from the University of California, San Francisco are the Jurkat T-cell line, U937, THP-1, FRO, HL60, and HUT78. These cell lines may also be available from other sources.

Monoclonal Antibodies: AIIB2, against human $\beta1$ integrin (the "anti-$\beta$-1"), is available from Dr. Caroline Damsky, Department of Oral Biology, University of California, San Francisco. HP2/1, against the VCAM-1-binding domain of VLA-4 (the "anti-$\alpha$-4") was purchased from AMAC, Inc. (Westbrook Me., Product #0764). The AP2/1 also cross-reacts with murine lymphocytes. P4H9, against human $\beta2$ integrin (the "anti-$\beta$-2") was purchased from Telios, Inc. (San Diego, Calif. Product #A052). This anti-$\beta$-2, against the $\beta$-2 integrin is not known to react with any subunit of VLA-4.

When used to treat lymphocytes, the anti-$\beta$-1 hybridoma supernatant was used at a 1:2 dilution. The anti-$\alpha$-4 antibody was purified by the manufacturer, and used at a 5 $\mu$g/ml concentration. The anti-$\beta$-2 was purified by the manufacturer, and used at 5 $\mu$g/ml. For treatment of lymphocytes, the lymphocytes were mixed with the above concentrations of antibody, and allowed to incubate on ice for a about 30 minutes prior to use. The cells were washed to remove unbound antibody, and resuspended in RPMI to a typical concentration of $10^7$ cells/ml.

Other tissue sections: In the in vitro frozen brain section assay, the preparation of brain sections is described below. Lymph node and intestinal tissues were removed from rats, and sectioned as described for brain tissues, below.

A. In Vitro Frozen Brain Section Assay

In order to establish inflammatory brain lesions that involve a large degree of immune cell infiltration, rats were injected in the brain with human kidney cell line 293 (American Type Culture Collection, "ATCC," 1573). This method was found to stimulate the entry of all leukocyte classes into the brain in a predictable time course. The trauma of the injection induces the entry of neutrophils and monocytes within minutes, which continues for about 24 to about 48 hours. The presence of the human cells serves as a persistent irritant to the immune system, stimulating further leukocyte infiltration, including that of lymphocytes. Typically, by about day 6, lymphocytes and monocytes are the major infiltrating leukocyte classes, entering in such large numbers so as to produce cellular cuffs around small blood vessels in the brain near the injection site. The speed and predictability of this procedure has made it ideal for obtaining brain tissue that can be used in the in vitro assay described below. In this assay, the brains are quickly frozen and sectioned. Leukocytes (immortalized and grown as cell lines, or freshly isolated from rodents or humans as described above) are then exposed to the sections, and, if they express the appropriate receptors, adhere selectively to the exposed profiles of activated endothelium near the inflammatory lesion. The leukocytes do not bind to nonactivated endothelium in the brain sections away from the inflammatory lesion or within sections of the non-stimulated control brain.

Rats (male Sprague-Dawley, 275–300 g), were anesthetized with Nembutal (60 mg/kg-i.p.) and mounted in a stereotaxic device. The head was shaved and an incision was made to reveal the dorsal skull. Holes were drilled through the skull on the left and right side overlying the parietal cortex. $10^7$ human kidney derived cells (ATCC 1573 cell line), suspended in PBS, were delivered to the parietal cortices in a volume of 10 $\mu$l. It is believed that other allogeneic cells or cell lines would also induce the present MS-type symptoms via these methods. For example, we have used primary bovine microvascular endothelial cells to induce a similar inflammatory reaction.

The incision was sutured and the animal allowed to recover for 1–10 days. On the appropriate day, brains were removed from animals that had been anesthetized with halothane and killed by cardiac puncture. The cerebellum was removed and the brains were then placed rostral side down on a mound of gum tragacanth (mixed with water to the consistency of thick paste) and frozen by immersion for 60 seconds in 2-methyl butane chilled on dry ice. The brains were then stored in sealed tubes at −80° C.

Immediately before the assay, 10 micron thick brain sections were cut on a cryostat and transferred to the center of a 14 mm well, pre-formed within a thin epoxy coating (Catalog #100314, Carlson Scientific, Inc., Peotone, Ill.) and allowed to air-dry at room temperature. The transfer was accomplished by touching the slide (at room temperature) to the section, which was still on the cold knife blade. Sections of control tissues (peripheral lymph nodes and Peyer's patches, isolated from noninjected rats, frozen and stored as described above) were usually placed adjacent to the brain sections in the same wells. The slides were positioned on a metal tray resting on ice and the wells were filled with 100 $\mu$l of the appropriate cell suspension. The metal tray and supporting ice were then gyrated at about 50- about 80 rpm for 30 minutes on an orbital shaker (Lab Line Instruments, Inc., Model 3520, with 1 inch diameter rotation). The cell suspension was then decanted and the slides were carefully placed vertically in PBS with 2.5% glutaraldehyde on ice for 20 minutes. The slides were then dipped 5 times in PBS, placed in 0.5% toluidine blue (20% EtOH) for 1 minutes, destained with 2 brief dips in 100% ethanol, covered with Immu-mount TM mounting medium (Shandon, Sweickley, Pa.), and cover slipped.

Herein, cell suspensions used were freshly isolated rat, mouse or human lymphocytes, the U937T human myelomonocytic cell line, and the Jurket human T cell line. Cell lines THP-1, FRO, HL60 and HUT78 were found not to bind with stimulated brain sections, and were not further analyzed in the brain section assay.

The degree of lymphocyte binding was quantified by one of two methods. The first relied upon an internal reference population of cells, similar to that described by Butcher, et al., *J.Immunol* 123: 1996–2003 (1979). The second method was based on the absolute number of lymphocytes bound to blood vessels in a given tissue section. For the internal reference method, populations of lymphoid cell lines were mixed with freshly isolated lymphocytes of a different species (e.g. human cell lines with mouse lymphocytes) so that both were at a final concentration of $3-5 \times 10^{-7}$/ml. Aliquots of the mixed population were then treated with species-specific antibodies for 30 minutes on ice. In general, the cells were washed out of the antibody prior to the binding assay. Binding was quantified by determining the ratio of two different populations of leukocytes bound to blood vessels. It was always arranged such that the leukocyte populations could readily be distinguished by size—lymphoid cell lines are large cells, generally greater than 20 μm in diameter, while lymphocytes are small cells, less than 10 μm in diameter. Thus in an experiment with human T cell line mixed with rat lymphocytes, the degree of inhibition produced by an anti-human monoclonal antibody (compared to control antibodies or to no treatment) was quantified by determining the ratio of large to small cells bound. The results obtained are presented in Table 12, below. As can be seen, use of an anti-VLA-4 reagent significantly inhibited binding of immune cells to brain cells displaying MS-type inflammation. These results are also shown in FIG. 10, which clearly displays the inhibitory effect of the anti-VLA-4 reagents.

TABLE 12

Quantification of rat lymphocyte binding to different tissue sections by comparing the number of lymphocytes bound to all vessels under treated and untreated conditions. Four replicates were used for each treatment, and raw data are presented in parenthesis below the mean.

| Treatment | Brain | Intestinal | Lymph Node |
|---|---|---|---|
| No treatment | 24 (100%) (24/24/32/18) | 43 (100%) (35/45/42/50) | 21 (100%) (25/27/18/15) |
| anti-VLA-α | 2 (8%) (2/3/2/2) | 6 (15%) (3/3/5/10) | 20 (95%) (14/30/22/12) |

The second method of quantification compared a single population of leukocytes treated in different ways in adjacent assay wells. The degree of inhibition was determined by comparing the number of leukocytes bound to all vessels in a given tissue section under treated and untreated conditions. Tissue sections were prepared as described above. The degree of binding was quantified as the actual number of cells bound to the blood vessels within the sections. These data are presented in Table 13, below.

In addition, lymph node tissue was also tested, and these data are displayed in FIG. 11. All reagents were prepared as described above. Here, anti-β-1 antibody and anti-α-4 antibody were both shown to inhibit Jurkat T-cell lymphocyte binding to brain sections, but not to lymph node sections.

These data confirm that anti-VLA-4 reagents showed substantial inhibition of leukocyte binding to brain tissue displaying the features of MS-type inflammation.

TABLE 13

| Treatment Used | Ratio large/small | % Control Jurkat Binding |
|---|---|---|
| No treatment | 2.08 ± 0.17 | 100 ± 8 |
| anti-β-1 | 0.02 ± 0.01 | 1 ± 0.5 |
| anti-α-4 | 0.23 ± 0.15 | 11 ± 7 |

B. Leukocyte Binding to Cultures of Blood Brain Barrier Endothelial Cells

Bovine or human brain endothelial cells were maintained in accordance with the blood brain barrier model as described in the present specification. In experiments where the endothelium was activated, 5 μl of stimulating agent was added directly to the lower chamber medium (800 μl) of the culture system. Here, TNFα (Amgen Biologicals, Thousand Oaks, Calif.) was added to the lower chamber for a final concentration of 400 μ/ml. In activation, PMA-S (in DMSO) was found not to be effective in stimulating lymphocyte binding, but other activating agents are known, and will be apparent to those skilled in the art.

In this manner, the endothelial cells were exposed to the agent on their ablumenal surface, as would be the typical situation during an inflammatory reaction in the brain. Immediately before the assay, the electrical resistance of the cultures was measured and the filters (supporting the endothelial cells) were washed at room temperature by dipping in three separate vats of D-MEM with 1% FBS and 20 mM Hepes (200 mls. each). The filters were then placed in fresh wells containing the same medium and the assay was performed at room temperature.

Typically, 10 μl of leukocytes (at a preferred concentration of $10^7$/ml) in the presence or absence of test reagents, were added to the upper chamber of the culture system, such that the leukocytes would encounter the lumenal or blood side of the endothelium, as they would in the brain vasculature. Here, leukocytes were rat, mouse or human lymphocytes, the U93T human myelomonocytic cell line, and the Jurket human T cell line as described above. The lymphocytes were pretreated with anti-β-1 or anti-β-2 antibody as described above.

Cell lines THP-1 and FRO were also found to bind to brain endothelial stimulated with TNFα, but HL60 and HUT78 did not so bind. U937 binding was found not to be inhibited by exposure to anti-β-1.

The culture plates were placed on a gyratory shaker at about 100 rpm for 30 seconds, then allowed to sit undisturbed at room temperature for about 30 minutes. The assay was terminated by gently washing the filters in PBS with 1% glutaraldehyde (dipping and pouring three times at different angles). The glutaraldehyde causes the cells to fluoresce under the proper optical conditions, as described below. The filters were then allowed to fix in the glutaraldehyde solution undisturbed for 60 minutes.

The degree of leukocyte binding to the filters was examined in one of two ways. In the first, the bound cells were visualized directly. The filter was cut free of the culture well apparatus and mounting on glass slides with Immu-mount ™. The filters were examined with an immunofluorescence microscope set for rhodamine or fluorescein optics, and observing the cells by glutaraldehyde-induced autofluorescence.

The results of the immunofluorescence assay can be visualized in FIG. 8. As is easily visualized, the density of Jurkat T-cell lymphocytes pretreated with anti-β-1 antibody is far lower (Panel A) than the binding density for untreated leukocytes (Panel B). This graphically depicts the anatomical and physiological reaction when a reagent is used to block the VCAM-1/VLA-4 interaction between brain endothelial cells and leukocytes.

In the second method, the leukocytes were prelabeled with a radioactive tracer and the degree of binding was quantified by measuring the amount of radioactivity associated with the entire endothelial surface on the culture filter. Prelabeling of lymphoid cell lines was accomplished by the addition of 1 uCi/ml 125IUDR (Amersham #XX) obtained from the Amersham Corporation, Arlington Heights, Ill., to the standard culture medium approximately 12–20 hrs. before the assay. The cells were washed free of unincorporated label by three separate washes in 15 mls of fresh bench medium (RPMI-1640 with 5% FBS and 25 mM Hepes). Concentration was then adjusted to $10^7$ cells/ml in the presence or absence of test reagents. Again, all of the above lymphocytes were used (rat, mouse or human lymphocytes, the U937T human myelomonocytic cell line, and the Jurket human T cell line) as described above. The lymphocytes were pretreated with anti-β-1 or anti-β-2 antibody as described above. Also, the lymphocytes were pretreated with anti-VLA-α-4 as described above.

The assay was carried out as above, except that at the end the isolated filters are placed in tubes and counted in a gamma counter (Beckman Corporation, Model 5500B) for 1 minute. The results are presented in Table 14 below. As can be seen, the samples that contained anti-VLA-4 reagents show far lower radioactivity levels the controls. These data confirm the results from the above fluorescence data, namely, that the binding of anti-VLA-4 to the VCAM-1 receptor is substantially inhibited by reagents which would prevent binding at that locus.

These data are also presented at FIG. 11 which shows the relative degree of Jurkat T-cell lymphocyte binding to brain endothelial cells in the BBB system. As can easily be seen, the anti-β-1 antibody effectively inhibited the binding of leukocytes to TNF-α brain endothelial cells. Anti-β-2, as a control, on the other hand, approaches the untreated control. Plainly, the β-1 subunit provides an effective target for preventing VLA-4/VCAM-1 interaction in the brain.

TABLE 14

This table shows the quantification of lymphocyte binding via radioactive labelling of lymphocytes.

| Lymphocyte Type | Treatment | Count per Minute |
| --- | --- | --- |
| Jurkat T-cell | 0 (no TNFα) | 112; 273 |
| | anti-β-1 (no TNFα) | 259; 156 |
| | anti-β-2 (no TNFα) | 198; 124 |
| | 0 (+ TNFα) | 1430; 1150 |
| | anti-β-1 (+ TNFα) | 361; 385 |
| | anti-β-2 (+ TNFα) | 1313; (n/a) |

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. An in vitro model of a blood-brain barrier, comprising a porous solid support upon which is disposed an essentially confluent monolayer of brain microvascular endothelial cells, a growth medium and an agent that effectively increases cyclic AMP concentrations in said cells such that peripheral phalloidin staining is substantially present.

2. A model as recited in claim 1, wherein said endothelial cells are mixed endothelial cells.

3. A model as recited in claim 1, wherein said porous solid support is a porous filter or membrane of a material selected from the group consisting of polycarbonate, nitrocellulose, cellulose, collagen and fiberglass.

4. A model as recited in claim 1, further comprising an extracellular matrix material disposed upon said porous solid support, interposed between said endothelial cells and said porous solid support.

5. A model as recited in claim 4, wherein said extracellular matrix material is selected from the group consisting of astrocyte extracellular matrix, laminin, vitronectin, fibronectin, collagen, and Matrigel TM.

6. A model as recited in claim 1, wherein said agent is selected from the group consisting of agents that increase cell adenylate cyclase activity, agents that inhibit the degradation of intracellular cyclic AMP, and derivatives of cyclic AMP to which endothelial cells are permeable and which act physiologically as does cyclic AMP.

7. An in vitro model of a blood-brain barrier as recited in claim 1, further comprising an essentially confluent monolayer of brain astrocytes disposed on a side of said porous solid support opposite the side on which are disposed said endothelial cells.

8. An in vitro model of a blood-brain barrier as recited in claim 1, further comprising an essentially confluent monolayer of brain astrocytes disposed on a second surface other than the porous solid support upon which is disposed a monolayer of endothelial cells, in contact with said growth medium to which the endothelial cells are also exposed.

9. A model as recited in claim 1, wherein said porous solid support comprises microcarrier beads.

10. A model as recited in claim 9, further comprising an extracellular matrix material disposed on said beads, interposed between said beads and said endothelial cells.

11. A model as recited in claim 10, wherein said extracellular matrix material is selected from the group consisting of astrocyte extracellular matrix, laminin, vitronectin, fibronectin, collagen, and Matrigel ®.

12. A model as recited in claim 1, wherein said porous solid support comprises a tubular hollow fiber.

13. A model as recited in claim 12, further comprising an extracellular matrix material disposed on said hollow fiber, interposed between said hollow fiber and said endothelial cells.

14. A model as recited in claim 13, wherein said extracellular matrix material is selected from the group consisting of astrocyte extracellular matrix, laminin, vitronectin, fibronectin, collagen, and Matrigel ®.

15. A model as recited in claim 1, wherein E-cadherin is substantially present between endothelial cells.

16. An in vitro model of a blood-brain barrier, comprising a porous solid support upon which is disposed a confluent monolayer of brain microvascular endothelial cells, a growth medium and an agent that effectively increases cyclic AMP concentrations in said cells, such that the transmonolayer resistance is at least about 200 ohm-cm$^2$.

17. A model as recited in claim 16, wherein said endothelial cells are mixed or cloned endothelial cells.

18. A model as recited in claim 16, wherein said porous solid support is a porous filter or membrane of a material selected from the group consisting of polycarbonate, nitrocellulose, cellulose, collagen and fiberglass.

19. A model as recited in claim 16, further comprising an extracellular matrix material disposed upon said porous solid support interposed between said endothelial cells and said porous solid support.

20. A model as recited in claim 19, wherein said extracellular matrix material is selected from the group consisting of astrocyte extracellular matrix, laminin, vitronectin, fibronectin, collagen, and Matrigel ®.

21. A model as recited in claim 16, wherein said agent is selected from the group consisting of agents that increase cell adenylate cyclase activity, agents that inhibit the degradation of intracellular cyclic AMP, and derivatives of cyclic AMP to which endothelial cells are permeable and which act physiologically as does cyclic AMP.

22. An in vitro model of a blood-brain barrier as recited in claim 16, further comprising an essentially confluent monolayer of brain astrocytes disposed on a side of said porous solid support opposite the side on which are disposed said endothelial cells.

23. An in vitro model of a blood-brain barrier as recited in claim 16, further comprising an essentially confluent monolayer of brain astrocytes disposed on a second surface other than the porous solid support upon which is disposed a monolayer of endothelial cells, in contact with said growth medium to which the endothelial cells are also exposed.

24. A model as recited in claim 16, wherein said porous solid support comprises a tubular hollow fiber.

25. A model as recited in claim 24, further comprising an extracellular matrix material disposed on said hollow fiber, interposed between said hollow fiber and said endothelial cells.

26. A model as recited in claim 25, wherein said extracellular matrix material is selected from the group consisting of astrocyte extracellular matrix, laminin, vitronectin, fibronectin, collagen, and Matrigel ®.

27. A model as recited in claim 16, wherein E-cadherin is substantially present between endothelial cells.

28. An in vitro model of a blood-brain barrier comprising a porous solid support upon which is disposed an essentially confluent monolayer of brain microvascular endothelial cells, a growth medium and an agent that effectively increases cyclic AMP concentrations in said cells, wherein said growth medium is a cell-derived conditioned medium, a medium supplemented with a cell extract or a medium supplemented with a tissue extract, such that peripheral phalloidin staining is substantially present.

29. A model as recited in claim 28, wherein said endothelial cells are mixed or cloned endothelial cells.

30. A model as recited in claim 28, wherein said porous solid support is a porous filter or membrane of a material selected from among the group consisting of polycarbonate, nitrocellulose, cellulose, collagen and fiberglass.

31. A model as recited in claim 28, further comprising an extracellular matrix material disposed upon said porous solid support interposed between said endothelial cells and said porous solid support.

32. A model as recited in claim 31, wherein said extracellular matrix is selected from among the group consisting of astrocyte extracellular matrix, laminin, vitronectin, fibronectin, collagen, and Matrigel ®.

33. A model as recited in claim 28, wherein said agent is selected from the group consisting of agents that increase cell adenylate cyclase activity, agents that inhibit the degradation of intracellular cyclic AMP, and derivatives of cyclic AMP to which endothelial cells are permeable and which act physiologically as does cyclic AMP.

34. A model as recited in claim 28 wherein said cell-derived conditioned medium is endothelial cell-derived conditioned medium or astrocyte-derived conditioned medium.

35. An in vitro model of a blood-brain barrier as recited in claim 28, further comprising an essentially confluent monolayer of brain astrocytes disposed on a side of said porous solid support opposite the side on which are disposed said endothelial cells.

36. An in vitro model of a blood-brain barrier as recited in claim 28, further comprising an essentially confluent monolayer of brain astrocytes disposed on a second surface other than the porous solid support upon which is disposed a monolayer of endothelial cells, in contact with said growth medium to which the endothelial cells are also exposed.

37. A model as recited in claim 28, wherein said porous solid support comprises microcarrier beads.

38. A model as recited in claim 37, further comprising an extracellular matrix material disposed on said beads, interposed between said beads and said endothelial cells.

39. A model as recited in claim 38, wherein said extracellular matrix material is selected from the group consisting of astrocyte extracellular matrix, laminin, vitronectin, fribronectin, collagen, and Matrigel ®.

40. A model as recited in claim 28, wherein said porous solid support comprises a tubular hollow fiber.

41. A model as recited in claim 40, further comprising a of an extracellular matrix material disposed on said hollow fiber, interposed between said hollow fiber and said endothelial cells.

42. A model as recited in claim 41, wherein said extracellular matrix material is selected from the group consisting of astrocyte extracellular matrix, laminin, vitronectin, fibronectin, collagen, and Matrigel ®.

43. A model as recited in claim 28, wherein E-cadherin is substantially present between endothelial cells.

44. An in vitro model of a blood-brain barrier comprising a porous solid support upon which is disposed a confluent monolayer of brain microvascular endothelial cells, a growth medium and an agent that effectively increases cyclic AMP concentrations in said cells, wherein said growth medium is a cell-derived conditioned medium, a medium supplemented with a cell extract or a medium supplemented with a tissue extract, such that peripheral phalloidin staining is substantially present, and said monolayer has a transmonolayer resistance of at least about 200 ohm-cm$^2$.

45. A model as recited in claim 44, wherein said endothelial cells are mixed or cloned endothelial cells.

46. A model as recited in claim 44, wherein said porous solid support is a porous filter or membrane of a material selected from among the group consisting of polycarbonate, nitrocellulose, cellulose, collagen and fiberglass.

47. A model as recited in claim 44, further comprising an extracellular matrix material disposed upon said porous solid support, interposed between said endothelial cells and said porous solid support.

48. A model as recited in claim 47, wherein said extracellular matrix material is selected from among the group consisting of astrocyte extracellular matrix, laminin, vitronectin, fibronectin, collagen, and Matrigel ®.

49. A model as recited in claim 44, wherein said agent is selected from the group consisting of agents that increase cell adenylate cyclase activity, agents that inhibit the degradation of intracellular cyclic AMP, and derivatives of cyclic AMP to which endothelial cells are permeable and which act physiologically as does cyclic AMP.

50. A model as recited in claim 44 wherein said cell-derived conditioned medium is endothelial cell-derived or astrocyte-derived conditioned medium.

51. An in vitro model of a blood-brain barrier as recited in claim 44, further comprising an essentially confluent monolayer of brain astrocytes disposed on a side of said porous solid support opposite the side on which are disposed said endothelial cells.

52. An in vitro model of a blood-brain barrier as recited in claim 44, further comprising an essentially confluent monolayer of brain astrocytes disposed on a second surface other than the porous solid support upon which is disposed a monolayer of endothelial cells, in contact with said growth medium to which the endothelial cells are also exposed.

53. A model as recited in claim 44, wherein said porous solid support comprises a tubular hollow fiber.

54. A model as recited in claim 53, further comprising an extracellular matrix material disposed on said hollow fiber, interposed between said hollow fiber and said endothelial cells.

55. A model as recited in claim 54, wherein said extracellular matrix material is selected from the group consisting of astrocyte extracellular matrix, laminin, vitronectin, fibronectin, collagen, and Matrigel ®.

56. A model as recited in claim 44, wherein E-cadherin is substantially present between endothelial cells.

57. An in vitro model of a blood-brain barrier, comprising a porous solid support upon which is disposed a confluent monolayer of brain microvascular endothelial cells, a growth medium and an agent that effectively increases cyclic AMP concentrations in said cells such that peripheral phalloidin staining is substantially present, and said monolayer has a transmonolayer electric resistance of at least about 200 ohm-cm$^2$.

58. A model as recited in claim 57, wherein said endothelial cells are mixed endothelial cells.

59. A model as recited in claim 57, wherein said solid support is a porous filter or membrane of a material selected from the group consisting of polycarbonate, nitrocellulose, cellulose, collagen and fiberglass.

60. A model as recited in claim 57, further comprising an extracellular matrix material disposed upon said porous solid support interposed between said endothelial cells and said porous solid support.

61. A model as recited in claim 60, wherein said extracellular matrix material is selected from the group consisting of astrocyte extracellular matrix, laminin, vitronectin, fibronectin, collagen, and Matrigel ®.

62. A model as recited in claim 57, wherein said agent is selected from the group consisting of agents that increase cell adenylate cyclase activity, agents that inhibit the degradation of intracellular cyclic AMP, and derivatives of cyclic AMP to which endothelial cells are permeable and which act physiologically as does cyclic AMP.

63. An in vitro model of a blood-brain barrier as recited in claim 57, further comprising an essentially confluent monolayer of brain astrocytes disposed on a side of said porous solid support opposite the side on which are disposed said endothelial cells.

64. An in vitro model of a blood-brain barrier as recited in claim 57, further comprising an essentially confluent monolayer of brain astrocytes disposed on a second surface other than the porous solid support upon which is disposed a monolayer of endothelial cells, in contact with said growth medium to which the endothelial cells, are also exposed.

65. A model as recited in claim 57, wherein said porous solid support comprises a tubular hollow fiber.

66. A model as recited in claim 65, further comprising an extracellular matrix material disposed on said hollow fiber, interposed between said hollow fiber and said endothelial cells.

67. A model as recited in claim 66, wherein said extracellular matrix material is selected from the group consisting of astrocyte extracellular matrix, laminin, vitronectin, fibronectin, collagen, and Matrigel ®.

68. A model as recited in claim 57, wherein E-cadherin is substantially present between endothelial cells.

69. An in vitro model of a blood-brain barrier, comprising a porous solid support upon which is disposed a confluent monolayer of brain microvascular endothelial cells, a growth medium and an agent that effectively increases cyclic AMP concentrations in said endothelial cells, wherein said growth medium is a cell-derived conditioned medium, a medium supplemented with a cell extract or a medium supplemented with a tissue extract, such that the transmonolayer electrical resistance is at least about 200 ohm-cm$^2$.

70. A model as recited in claim 69, wherein said endothelial cells are mixed or cloned endothelial cells.

71. A model as recited in claim 69, wherein said porous solid support is a porous filter or membrane of a material selected from the group consisting of polycarbonate, nitrocellulose, cellulose, collagen and fiberglass.

72. A model as recited in claim 69, further comprising an extracellular matrix material disposed upon said porous solid support interposed between said endothelial cells and said porous solid support.

73. A model as recited in claim 72, wherein said extracellular matrix material is selected from the group consisting of astrocyte extracellular matrix, laminin, vitronectin, fibronectin, collagen, and Matrigel ®.

74. A model as recited in claim 69, wherein said agent is selected from the group consisting of agents that increase cell adenylate cyclase activity, agents that inhibit the degradation of intracellular cyclic AMP, and derivatives of cyclic AMP to which endothelial cells are permeable and which act physiologically as does cyclic AMP.

75. A model as recited in claim 69, wherein said cell-derived conditioned medium is endothelial cell-derived or astrocyte-derived conditioned medium.

76. An in vitro model of a blood-brain barrier as recited in claim 69, further comprising an essentially confluent monolayer of brain astrocytes disposed on a side of said porous solid support opposite the side on which are disposed said endothelial cells.

77. An in vitro model of a blood-brain barrier as recited in claim 69, further comprising an essentially confluent monolayer of brain astrocytes disposed on a second surface other than the porous solid support upon which is disposed a monolayer of endothelial cells, in contact with said growth medium to which the endothelial cells are also exposed.

78. A model as recited in claim 69, wherein said porous solid support comprises a tubular hollow fiber.

79. A model as recited in claim 78, further comprising an extracellular matrix material disposed on said hollow fiber, interposed between said hollow fiber and said endothelial cells.

80. A model as recited in claim 79, wherein said extracellular matrix material is selected from the group consisting of astrocyte extracellular matrix, laminin, vitronectin, fibronectin, collagent, and Matrigel ®.

81. A model as recited in claim 69, wherein E-cadherin is substantially present between endothelial cells.

* * * * *

UNITED STATES PATENT AND TRADEMARK OFFICE
CERTIFICATE OF CORRECTION

PATENT NO. : 5,260,210
DATED : Nov. 9, 1993
INVENTOR(S) : Rubin et al.

It is certified that error appears in the above-indentified patent and that said Letters Patent is hereby corrected as shown below:

On the title page, section [76], please delete Theodore A. Yednick as an inventor.

At column 1, line 3, please insert the following paragraph:
-- This invention was made in part with Government support under Grant No. R44-GM42268, a Small Business Innovation Research Award, issued by the United States Department of Health and Human Services. The government may have certain rights in this invention. --

In column 1, line 5, please delete "097/413,274" and insert therefore --07/413,274--.

In column 21, line 35, please delete "00" and insert therefore --200--.

In column 36, line 40 (claim 41), please delete "a of".

In column 40, line 6 (claim 80), please delete "collagent" and insert therefore --collagen--.

Signed and Sealed this

Fifteenth Day of November, 1994

Attest:

BRUCE LEHMAN

*Attesting Officer*   *Commissioner of Patents and Trademarks*